(12) United States Patent
Konetzki et al.

(10) Patent No.: US 9,505,724 B2
(45) Date of Patent: Nov. 29, 2016

(54) 4-AMINO SUBSTITUTED CONDENSED PYRIMIDINE COMPOUNDS AS PDE4 INHIBITORS

(71) Applicant: GRÜNENTHAL GMBH, Aachen (DE)

(72) Inventors: Ingo Konetzki, Aachen (DE); Florian Jakob, Aachen (DE); Tobias Craan, Aachen (DE); Christian Hesslinger, Zoznegg (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/817,683

(22) Filed: Aug. 4, 2015

(65) Prior Publication Data

US 2015/0353507 A1    Dec. 10, 2015

Related U.S. Application Data

(63) Continuation of application No. PCT/EP2014/000273, filed on Feb. 3, 2014.

(60) Provisional application No. 61/760,207, filed on Feb. 4, 2013.

(30) Foreign Application Priority Data

Feb. 4, 2013  (EP) ..................... 13000565

(51) Int. Cl.
| | | |
|---|---|---|
| A61K 31/517 | (2006.01) | |
| C07D 239/70 | (2006.01) | |
| C07C 53/18 | (2006.01) | |
| C07D 405/04 | (2006.01) | |
| C07D 239/94 | (2006.01) | |

(52) U.S. Cl.
CPC ........... *C07D 239/70* (2013.01); *A61K 31/517* (2013.01); *C07C 53/18* (2013.01); *C07D 239/94* (2013.01); *C07D 405/04* (2013.01)

(58) Field of Classification Search
CPC .......................... C07D 239/70; A61K 31/517
USPC ........................................ 544/253; 514/258.1
See application file for complete search history.

(56) References Cited

U.S. PATENT DOCUMENTS

| | | | |
|---|---|---|---|
| 5,712,298 A | 1/1998 | Amschler | |
| 7,723,348 B2 | 5/2010 | Hopper et al. | |
| 8,865,723 B2 | 10/2014 | Gurney et al. | |
| 9,018,175 B2 | 4/2015 | Flockerzi et al. | |
| 9,161,927 B2 | 10/2015 | Nickolaus et al. | |
| 9,221,843 B2 | 12/2015 | Gurney et al. | |
| 9,296,689 B2 | 3/2016 | Liu | |
| 2005/0004143 A1 | 1/2005 | Dugar et al. | |
| 2006/0293343 A1* | 12/2006 | Naganuma | C07D 405/04 514/256 |
| 2007/0155716 A1 | 7/2007 | Simmen et al. | |
| 2007/0259846 A1 | 11/2007 | Hoenke et al. | |
| 2009/0186875 A1 | 7/2009 | Hoenke et al. | |
| 2010/0197656 A1 | 8/2010 | Hoenke et al. | |

FOREIGN PATENT DOCUMENTS

| | | |
|---|---|---|
| WO | 95 01338 A1 | 1/1995 |
| WO | 2004 016596 A1 | 2/2004 |
| WO | 2004 087056 A2 | 10/2004 |
| WO | 2006 035061 A1 | 4/2006 |
| WO | 2006 111549 A1 | 10/2006 |

OTHER PUBLICATIONS

Schudt et al., "PDE Isoenzymes as Targets for Anti-Asthma Drugs"; European Respiratory Journal, 1995, vol. 8, pp. 1179-1183.
Mori, et al., "The human area postrema and other nuclei related to the emetic reflex express cAMP phosphodiesterases 4B and 4D"; Journal of Chemical Neuroanatomy, vol. 40, 2010, pp. 36-42.
Press, et al., "2 PDE4 Inhibitors—A review of the current field"; Progress in Medicinal Chemistry, vol. 47, 2009, pp. 37-74.
Robichaud, et al., "Deletion of phosphodiesterase 4D in mice shortens alpha2-adrenoceptor-mediated anesthesia, a behavioral correlate of emesis"; Journal of Clinical Investigation, vol. 110, No. 7, 2002, pp. 1045-1052.
Lee, et al., "Dynamic Regulation of Cystic Fibrosis Transmembrane Conductance Regulator by Competitive Interactions of Molecular Adaptors"; the Journal of Biological Chemistry, vol. 282, No. 14, Apr. 6, 2007, pp. 10414-10422.
Giembycz, "4D or not 4D- the emetogenic basis of PDE4 inhibitors uncovered?"; Trends in Pharmacological Sciences, vol. 23, No. 12, Dec. 2002, pp. 548.
Naganuma, et al., "Discovery of selective PDE4B inhibitors"; Bioorganic & Medicinal Chemistry Letters 19, 2009, pp. 3174-3176.

(Continued)

*Primary Examiner* — Kamal Saeed
*Assistant Examiner* — Janet L Coppins
(74) *Attorney, Agent, or Firm* — Norris McLaughlin & Marcus, P.A.

(57) ABSTRACT

The invention relates to novel substituted condensed pyrimidine compounds of general formula (I)

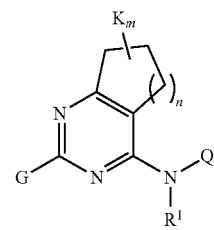

in which the chemical groupings, substituents and indices are as defined in the description, and to their use as medicaments, in particular as medicaments for the treatment of conditions and diseases that can be treated by inhibition of the PDE4 enzyme.

13 Claims, No Drawings

(56) References Cited

OTHER PUBLICATIONS

Goto et al., "Identification of the fused bicyclic 4-amino-2-phenylpyrimidine derivatives as novel and potent PDE4 inhibitors"; Bioorganic & Medicinal Chemistry Letters 23, No. 11, 2013, pp. 3325-3328.

Hill, et al.; "New Strategies for the Synthesis of Pyrimidine Derivatives"; Chemistry—A European Journal, vol. 14, 2008, pp. 6836-6844.

Bergmann; "Dehydration and Isomerization of Dimethylethynylcarbinol"; Journal of the Chimical Society, 1951, pp. 1218-1221.

Kralijevic, et al., "Synthesis, X-ray crystal structure study and antitumoral evaluations of 5,6-disubstituted pyrimidine derivatives"; Bioorganic & Medicinal Chemistry, vol. 18, 2010, pp. 2704-2712.

Wuts et al., "Protection for the carboxyl group"; Green't Protective Groups in Organic Synthesis, Fourth Edition, 2007, pp. 538-616.

Saldou, et al.; "Comparison of Recombinant Human PDE4 Isoforms: Interaction with Substrate and Inhibitors"; Cell. Signal. vol. 10, No. 6, 1998, pp. 427-440.

Schröter et al.; "Regioselective cross-coupling reactions of multiple halogenated nitrogen-, oxygen-, and sulfur-containing heterocycles"; Tetrahedron 61 (2005) pp. 2245-2267.

* cited by examiner

4-AMINO SUBSTITUTED CONDENSED PYRIMIDINE COMPOUNDS AS PDE4 INHIBITORS

The instant application is a Continuation of International Patent Application No. PCT/EP2014/000273, filed Feb. 3, 2014, which claims priority benefit under 35 U.S.C. §119(e) of U.S. Provisional Application No. 61/760,207, filed Feb. 4, 2013, and claims priority benefit under 35 U.S.C. §119(b) of European Application No. 13 000 565.5, filed Feb. 4, 2013.

The present invention relates to novel substituted, condensed pyrimidine compounds, and to their use as medicaments.

It is known that certain pyrimidine compounds are suitable for inhibiting specific phosphodiesterases (abbreviated as PDEs). Phosphodiesterases, or more accurately 3',5'-cyclonucleotide phosphodiesterases, are enzymes that catalyse the hydrolysis of the second messengers cAMP (cyclic adenosine monophosphate) and cGMP (cyclic guanosine monophosphate) to 5'-AMP (5'-adenosine monophosphate) and 5'-GMP (5'-guanosine monophosphate). Inhibition of phosphodiesterases thus represents a mechanism for modulating cellular processes and can be used to alleviate or cure disease conditions.

WO 95/01338 (A1), for example, describes how suitable PDE inhibitors can be used to treat inflammatory respiratory diseases, dermatoses, and other proliferative, inflammatory and allergic skin diseases. WO 95/01338 (A1) proposes, moreover, that such PDE inhibitors can find application in the treatment of diseases that are based on an excess release of TNF and leukotrienes, for example diseases from the arthritis spectrum (rheumatoid arthritis, rheumatoid spondylitis, osteoarthritis and other arthritic conditions). The international publication proposes, furthermore, the use of suitable PDE inhibitors as medicaments for diseases of the immune system (e.g. AIDS), symptoms of shock, as well as generalised inflammations in the gastrointestinal system (e.g. Crohn's disease and ulcerative colitis), diseases based on allergic and/or chronic, immunological adverse reactions in the upper respiratory tract (lateral pharyngeal space, nose) and adjacent regions (sinuses, eyes), such as for example allergic rhinitis/sinusitis, chronic rhinitis/sinusitis, allergic conjunctivitis and nasal polyps, but also diseases of the heart that can be treated by PDE inhibitors, such as for example heart failure, or diseases that can be treated because of the tissue-relaxing effect of PDE inhibitors, such as for example renal and ureteric colic in conjunction with kidney stones.

Phosphodiesterases are a group of enzymes encompassing 11 gene families (PDE1-11), which differ inter alia through their affinity to cAMP and cGMP.

The inhibition of the individual gene families with suitable substances is the subject of wide-ranging research. A known PDE5 inhibitor is sildenafil, which is commercially available under the trade name Viagra™ and which is used primarily for the treatment of erectile dysfunction.

The discovery that the second messenger cAMP plays an important role in many inflammatory processes and that PDE4 is strongly expressed in cells that control inflammation processes (see inter alia Schudt, C. et al. (1995). PDE isoenzymes as targets for anti-asthma drugs. European Respiratory Journal 8, 1179-1183), has led to the development of PDE4 inhibitors having an anti-inflammatory effect. One such PDE4 inhibitor having an anti-inflammatory effect is roflumilast for example (known under the trade name Daxas®), which was approved as a medicament for the treatment of COPD (chronic obstructive pulmonary disease). In addition to the desired anti-inflammatory effect of roflumilast, however, side-effects such as for example nausea, diarrhoea and headaches are observed, which limit the dose in humans.

Undesired side-effects in humans were observed with other PDE4 inhibitors too, so the therapeutic range (therapeutic window) of such medicaments is relatively narrow. The provision of PDE4 inhibitors having few side-effects and a better therapeutic window would therefore be desirable.

Phosphodiesterase 4 (PDE4) is cAMP-specific and encompasses 4 different subtypes (PDE4A, PDE4B, PDE4C and PDE4D). As is described below, efforts are being made to find subtype-selective PDE4 inhibitors, above all PDE4B-selective inhibitors, that have less severe or no side-effects, such that the therapeutic range of these compounds is increased significantly.

The inhibition of PDE4D is associated with the occurrence of undesired side-effects, such as for example diarrhoea, vomiting and nausea (see in this regard Mori, F. et al. (2010). The human area postrema and other nuclei related to the emetic reflex express cAMP phosphodiesterases 4B and 4D. Journal of Chemical Neuroanatomy 40, 36-42; Press, N.J.; Banner K. H (2009). PDE4 inhibitors—A review of the current field. Progress in Medicinal Chemistry 47, 37-74; Robichaud, A. et al. (2002). Deletion of phosphodiesterase 4D in mice shortens a2-adrenoceptor-mediated anesthesia, a behavioral correlate of emesis. The Journal of Clinical Investigation 110, 1045-52; or Lee et al., (2007). Dynamic regulation of CFTR by competitive interactions of molecular adaptors. Journal of Bio logical Chemistry 282, 10414-10422); or Giembycz, M. A. (2002). 4D or not 4D—the emetogenic basis of PDE4 inhibitors uncovered? Trends in Pharmacological Sciences 23, 548).

In an article entitled "Discovery of selective PDE4B inhibitors" published in Bioorganic & Medicinal Chemistry Letters 19 (2009) p. 3174-3176, Kenji et al. disclose thirty-five pyrimidine compounds that exhibit PDE4B selectivity. Some of the compounds listed are said to show a 10-times or even higher inhibitory activity against PDE4B than against PDE4D.

The compounds examined by Kenji et al. are substantially encompassed by the general formula described in US 2006/0293343A1. US 2006/0293343A1 discloses specific pharmaceutically effective PDE4-inhibiting pyrimidine compounds having an anti-inflammatory effect, of the following general formula:

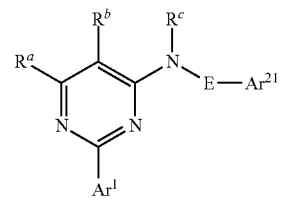

in which
Ar$^1$ denotes optionally substituted furyl, thienyl, triazolyl, thiazolyl, oxazolyl or benzothiazolyl;
E denotes a single bond or methylene;
Ar$^{21}$ denotes an optionally substituted phenyl or naphthyl;
R$^a$ and R$^b$ in each case independently of one another denotes hydrogen or alkyl, alkenyl, alkynyl, alkoxy, thioalkyl, alkyl sulfinyl, alkyl sulfonyl, each of which can optionally be substituted; and
R$^c$ denotes hydrogen or optionally substituted alkyl.

In the article by Kenji et al. the authors describe the examination of various structure-activity relationships, discussing inter alia the influence of the substituents at the 5- and 6-position on the pyrimidine ring (the substituent at the 5-position corresponds to $R^b$ in the general formula above, which was taken from US 2006/0293343A1, and the substituent at the 6-position corresponds to $R^a$). It can be inferred from the article that when an allyl, ethyl, cyano or formyl radical is bound at the 5-position of the pyrimidine ring, highly effective, selective PDE4B compounds were obtained. If, however, a larger chemical group is present at the same position, the inhibitory activity of the tested compounds decreases. With regard to possible modifications of the substituents at the 6-position of the pyrimidine ring, the authors ascertain that if methyl is replaced with ethyl at this position, the activity of the compound increases and the selectivity is lowered. Thus the authors reason that changes at the 5- and/or 6-position of the pyrimidine ring influence the activity and the selectivity of the pyrimidine compound. The authors allude to steric effects, without however giving any further information as to how the selectivity can be influenced without losing inhibitory activity.

Based on this prior art the object was now to find compounds that are preferably PDE4B-selective (i.e. to find active compounds that inhibit PDE4B to a greater extent and do not or scarcely inhibit the PDE4D subtype). The advantage of such a PDE4B selectivity, as mentioned above, is that various side-effects do not (should not) occur or occur only to a small extent and that therefore a greater therapeutic range (=therapeutic window) of the pharmaceutical active ingredient is (should be) obtained. The therapeutic range of a pharmaceutical active ingredient or medicament describes the gap between its therapeutic dose and a dose that would lead to a toxic or undesired effect. The greater the therapeutic range, the rarer or more unlikely the occurrence of certain toxic or undesired side-effects and hence the safer and more tolerable the pharmaceutical active ingredient or medicament. The therapeutic range is often also referred to as the therapeutic window or therapeutic index. These names are used synonymously in the present application.

The inventors have now found pyrimidine compounds that display the desired inhibiting and PDE4B-selective property and are superior to the corresponding pyrimidine compounds of the prior art. They are therefore particularly suitable for the treatment of diseases and conditions in which inhibition of the PDE4 enzyme, in particular the PDE4B enzyme, is advantageous.

The invention thus relates to pyrimidine compounds of the following formula (I)

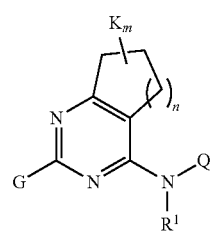

(I)

in which
G denotes a phenyl optionally substituted with at least one substituent Z or a 6-membered heteroaromatic optionally substituted with at least one substituent Z, or denotes a phenyl optionally substituted with at least one substituent Z or a 6-membered heteroaromatic optionally substituted with at least one substituent Z, being part of a 8- to 10-membered heterocyclic condensed ring containing at least one heteroatom selected from N, O, and S;

G preferably denotes a phenyl optionally substituted with at least one substituent Z or a 6-membered heteroaromatic optionally substituted with at least one substituent Z, selected from the following groups G1 to G9;

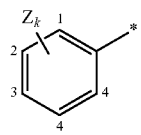
G1

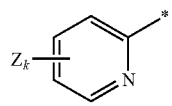
G2

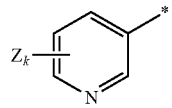
G3

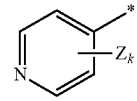
G4

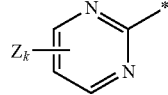
G5

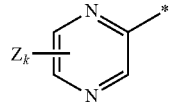
G6

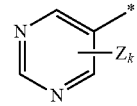
G7

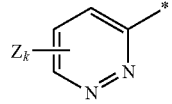
G8

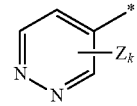
G9 in which the site marked with an asterisk (*) indicates the binding site at position 2 of the pyrimidine ring;

G particularly preferably denotes a phenyl optionally substituted with at least one substituent Z or a 6-membered heteroaromatic optionally substituted with at least one substituent Z, selected from G1, G2, G3 or G4; G most particularly preferably denotes G1;

Z independently of one another denotes ($C_1$-$C_6$) alkyl, ($C_1$-$C_6$) hydroxyalkyl, ($C_1$-$C_6$) alkoxy, ($C_1$-$C_6$) haloalkyl, ($C_1$-$C_6$) haloalkoxy, —S($C_1$-$C_6$) alkyl, halogen, hydroxyl or cyano, wherein aforementioned alkyls are branched or straight-chain and can be substituted; Z preferably independently of one another denotes $CH_3$, $OCH_3$, $CF_3$, $CHF_2$, $CH_2F$, $OCF_3$, $OCHF_2$, $OCH_2F$, $SCH_3$, Cl, F, OH or CN;

k denotes 0, 1, 2; k preferably denotes 0 or 1;

Q denotes a phenyl, pyrimidyl, or pyrazinyl group (preferably phenyl) which groups are substituted with a substituent $X^1$ and optionally substituted with at least one substituent X, in which $X^1$ is preferably bound in para-position; Q is preferably selected from the following groups Q1 to Q13,

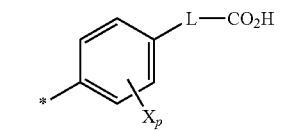
Q1

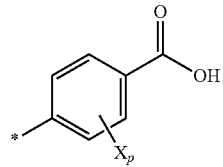
Q2

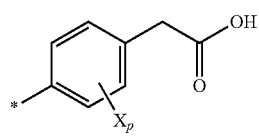
Q3

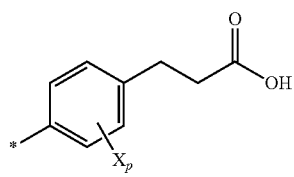
Q4

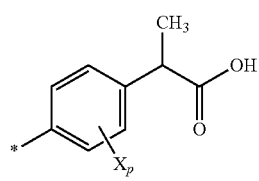
Q5

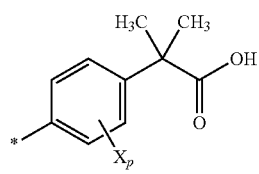
Q6

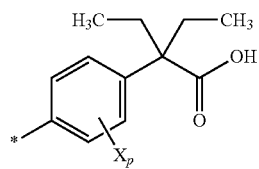
Q7

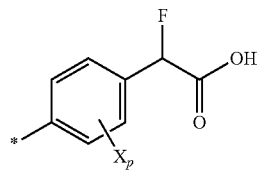
Q8

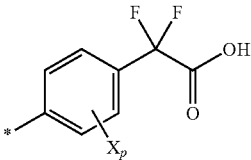
Q9

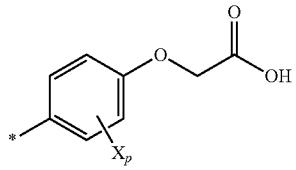
Q10

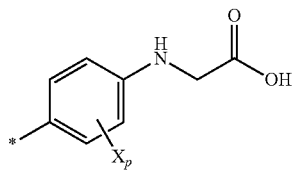
Q11

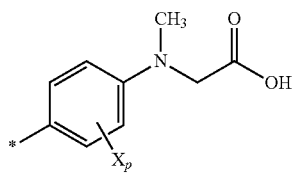
Q12

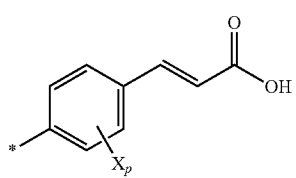
Q13 in which the site marked with an asterisk (*) indicates the binding site at the nitrogen;

p denotes 0, 1, 2, 3 or 4; p preferably denotes 0 or 1;

Q particularly preferably denotes the group Q2, Q3, Q8 or Q9; most particularly preferably the group Q2 or Q3;

X independently of one another denotes $(C_1-C_6)$ alkyl, $(C_3-C_6)$ cycloalkyl, $(C_1-C_6)$ alkoxy, $(C_3-C_6)$ cycloalkoxy, $(C_1-C_6)$ haloalkyl, $(C_1-C_6)$ haloalkoxy, halogen, hydroxyl, cyano, carboxyl, —$NH_2$, —$NH(C_1-C_6)$ alkyl, —$N((C_1-C_6)$ alkyl$)_2$, N-pyrrolidinyl, N-piperidinyl, N-morpholinyl, —NH—C(O)—$(C_1-C_6)$ alkyl, —C(O)—$NH_2$, —C(O)—NH$(C_1-C_6)$ alkyl, —C(O)—N$((C_1-C_6)$ alkyl$)_2$, —$S(O)_2$—$NH_2$, —S$(C_1-C_6)$ alkyl, —S(O)—$(C_1-C_6)$ alkyl, or —$S(O)_2$—$(C_1-C_6)$ alkyl, wherein the aforementioned alkyl chains are branched or straight-chain and can be substituted;

$X^1$ denotes an L-$CO_2R^2$ group;

L denotes a bond, $(C_1-C_6)$ alkylene, $(C_2-C_6)$ alkenylene, —O—$(C_1-C_4)$ alkylene, —NH—$(C_1-C_4)$ alkylene, or —$NR^3$—$(C_1-C_4)$ alkylene, wherein aforementioned alkylenes or alkenylenes can each be substituted with one or more halogen atoms (in particular fluorine) or wherein aforementioned alkylenes or alkenylenes can be substituted with one or more $(C_1-C_6)$ alkyl groups (preferably methyl or ethyl), or wherein in aforementioned alkylenes or alkenylenes a —$CH_2$ unit can be replaced by an oxygen atom;

L preferably denotes a bond or methylene, wherein the methylene can be substituted with one or two halogen atoms (in particular fluorine);

$R^1$ denotes hydrogen or a branched or straight-chain ($C_1$-$C_6$) alkyl (preferably ($C_1$-$C_4$) alkyl); $R^1$ preferably denotes hydrogen;
$R^2$ and $R^3$ independently of each other denote hydrogen or a branched or straight-chain ($C_1$-$C_6$) alkyl (preferably ($C_1$-$C_4$) alkyl);
n denotes 1 or 2;
K denotes ($C_1$-$C_6$) alkyl, preferably ($C_1$-$C_4$) alkyl, ($C_1$-$C_6$) alkoxy, preferably ($C_1$-$C_4$) alkoxy, ($C_1$-$C_6$) haloalkyl, preferably ($C_1$-$C_4$) haloalkyl, halogen, hydroxyl or cyano; and
m denotes 0, 1, 2, 3 or 4,
as well as pharmacologically tolerable salts, diastereomers, enantiomers, racemates, hydrates or solvates thereof.

Preferred compounds of general formula (I) are those of general formula (I'), in which G denotes G1:

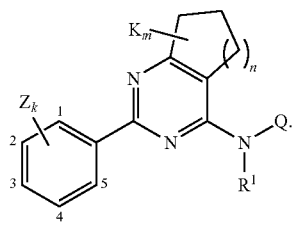
(I')

In an [embodiment A] the invention relates to pyrimidine compounds of general formula (I-A)

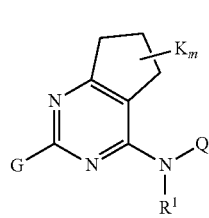
(I-A)

wherein in general formula (I-A) the chemical groupings G and Q and the substituents K and $R^1$ have the definitions described in connection with general formula (I) and wherein m denotes 0, 1 or 2, m preferably denoting 0 or 1. Preferred pyrimidine compounds of formula (I-A) are those in which Q denotes Q1, Q2 or Q3 and G denotes G1, G2, G3 or G4. Compounds of formula (I-A) as defined above in which G denotes G1 and $R^1$ denotes H are particularly preferred.

In an [embodiment B] the invention relates to pyrimidine compounds of general formula (I-B)

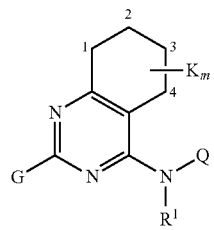
(I-B)

wherein in general formula (I-B) the chemical groupings G and Q and the substituents K and $R^1$ have the definitions described in connection with general formula (I) and wherein m denotes 0, 1 or 2, m preferably denoting 0 or 1. Preferred pyrimidine compounds of formula (I-B) are those in which Q denotes Q1, Q2 or Q3 and G denotes G1, G2, G3 or G4. Compounds of formula (I-B) as defined above in which G denotes G1 and $R^1$ denotes hydrogen are particularly preferred.

In an [embodiment C] the invention relates to pyrimidine compounds of general formula (I-C)

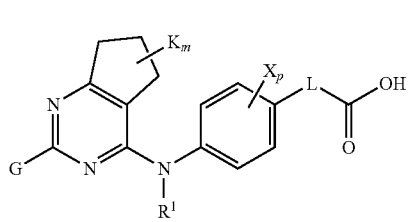
(I-C)

wherein in general formula (I-C) the chemical groupings G and L, the substituents K, X and $R^1$ and the index p have the definitions described in connection with general formula (I) and wherein m denotes 0, 1 or 2, m preferably denoting 0 or 1. Preferred pyrimidine compounds of formula (I-C) are those in which G denotes G1, G2, G3 or G4. Compounds of formula (I-C) as defined above in which G denotes G1 and $R^1$ denotes hydrogen are particularly preferred.

In an [embodiment D] the invention relates to pyrimidine compounds of general formula (I-D)

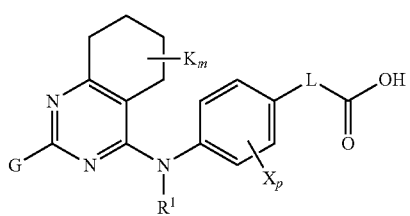
(I-D)

wherein in general formula (I-D) the chemical groupings G and L, the substituents K, X and $R^1$ and the index p have the definitions described in connection with general formula (I) and wherein m denotes 0, 1 or 2, m preferably denoting 0 or 1. Preferred pyrimidine compounds of formula (I-D) are those in which G denotes G1, G2, G3 or G4. Compounds of formula (I-D) as defined above in which G denotes G1 and $R^1$ denotes hydrogen are particularly preferred.

In an [embodiment E] the invention relates to pyrimidine compounds of general formula (I-E)

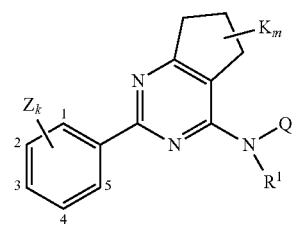
(I-E)

wherein in general formula (I-E) the chemical grouping Q and the substituents K, Z and R¹ have the definitions described in connection with general formula (I) and wherein m denotes 0, 1 or 2, m preferably denoting 0 or 1; and k denotes 0, 1, 2, 3, 4 or 5, k preferably denoting 1, 2 or 3. Preferred pyrimidine compounds of formula (I-E) are those in which Q denotes Q1, Q2 or Q3. Compounds of formula (I-E) as defined above in which Q denotes Q1 and R¹ denotes hydrogen, or in which Q denotes Q2 and R¹ denotes hydrogen, or in which Q denotes Q3 and R¹ denotes hydrogen are particularly preferred.

In an [embodiment F] the invention relates to pyrimidine compounds of general formula (I-F)

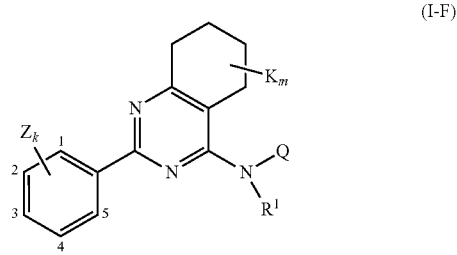

(I-F)

wherein in general formula (I-F) the chemical grouping Q and the substituents K, Z and R¹ have the definitions described in connection with general formula (I), wherein m denotes 0, 1 or 2, m preferably denoting 0 or 1; and k denotes 0, 1, 2, 3, 4 or 5, k preferably denoting 1, 2 or 3. Preferred pyrimidine compounds of formula (I-F) are those in which Q denotes Q1, Q2 or Q3. Compounds of formula (I-F) as defined above in which Q denotes Q1 and R¹ denotes hydrogen, or in which Q denotes Q2 and R¹ denotes hydrogen, or in which Q denotes Q3 and R¹ denotes hydrogen are particularly preferred.

If G stands for a phenyl optionally substituted with at least one substituent Z or a 6-membered heteroaromatic optionally substituted with at least one substituent Z, being part of a 8- to 10-membered heterocyclic condensed ring containing at least on heteroatom selected from N, O, and S, then the following structures G10-G13 are preferred

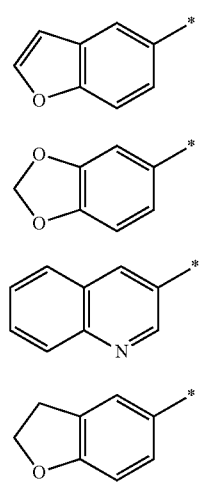

Consequently, the invention thus also relates to compounds of general formula (I-A) wherein in general formula (I-A) G stands for G10, G11, G12 or G13, the chemical grouping Q and the substituents K and R¹ have the definitions described in connection with general formula (I) and wherein m denotes 0, 1 or 2, m preferably denoting 0 or 1. Preferred pyrimidine compounds of formula (I-A) are those in which Q denotes Q1, Q2 or Q3 and G denotes G10, G11, G12 or G13.

The invention further relates to compounds of general formula (I-B) wherein in general formula (I-B) G stands for G10, G11, G12 or G13, the chemical grouping Q and the substituents K and R¹ have the definitions described in connection with general formula (I) and wherein m denotes 0, for 2, m preferably denoting 0 or 1. Preferred pyrimidine compounds of formula (I-B) are those in which Q denotes Q1, Q2 or Q3 and G denotes G 10, G11, G12 or G13.

The invention further relates to compounds of general formula (I-C) wherein in general formula (I-C) G stands for G10, G11, G12 or G13, the chemical grouping L, the substituents K, X and R¹ and the index p have the definitions described in connection with general formula (I) and wherein m denotes 0, 1 or 2, m, preferably denoting 0 or 1. Preferred pyrimidine compounds of formula (I-C) are those in which G denotes G10, G11, G12 or G13.

The invention further relates to compounds of general formula (I-D) wherein in general formula (I-D) G stands for G10, G11, G12 or G13, the chemical grouping L, the substituents K, X and R¹ and the index p have the definitions described in connection with general formula (I) and wherein m denotes 0, 1 or 2, m preferably denoting 0 or 1. Preferred pyrimidine compounds of formula (I-D) are those in which G denotes G10, G11, G12 or G13.

The invention further relates to compounds of general formula (I-E) wherein in general formula (I-E) G stands for G10, G11, G12 or G13, the chemical grouping Q and the substituents K, Z and R¹ have the definitions described in connection with general formula (I) and wherein m denotes 0, 1 or 2, m preferably denoting 0 or 1; and k denotes 0, 1, 2, 3, 4 or 5, k preferably denoting 1, 2 or 3. Preferred pyrimidine compounds of formula (I-E) are those in which Q denotes Q1, Q2 or Q3. Compounds of formula (I-E) as defined above in which Q denotes Q1 and R¹ denotes hydrogen, or in which Q denotes Q2 and R¹ denotes hydrogen, or in which Q denotes Q3 and R¹ denotes hydrogen are particularly preferred.

The invention further relates to compounds of general formula (I-F) wherein in general formula (I-F) G stands for G10, G11, G12 or G13, the chemical grouping Q and the substituents K, Z and R¹ have the definitions described in connection with general formula (1), wherein m denotes 0, 1 or 2, m preferably denoting 0 or 1; and k denotes 0, 1, 2, 3, 4 or 5, k preferably denoting 1, 2 or 3. Preferred pyrimidine compounds of formula (I-F) are those in which Q denotes Q1, Q2 or Q3. Compounds of formula (I-F) as defined above in which Q denotes Q1 and R¹ denotes hydrogen, or in which Q denotes Q2 and R¹ denotes hydrogen, or in which Q denotes Q3 and R¹ denotes hydrogen are particularly preferred.

Unless otherwise specified, the term $(C_1-C_6)$ alkyl is understood to mean branched and unbranched alkyl groups consisting of 1 to 6 hydrocarbon groups. Examples of $(C_1-C_6)$ alkyl radicals are methyl, ethyl, n-propyl, 1-methylethyl (isopropyl), n-butyl, 1-methylpropyl, 2-methylpropyl, 1,1-dimethylethyl (tert-butyl), n-pentyl, 1-methylbutyl, 2-methylbutyl, 3-methylbutyl, 1,1-dimethylpropyl, 1,2-dimethylpropyl, 2,2-dimethylpropyl, n-hexyl, 1-methylpentyl, 2-methylpentyl, 3-methylpentyl, 4-methylpentyl. ($C_1$-$C_4$) alkyl radicals are preferred, ($C_1$-$C_3$) alkyl radicals being particularly preferred, in particular methyl, ethyl and propyl. Unless otherwise stated, the definitions of propyl, butyl, pentyl and hexyl encompass all possible isomeric forms of the individual radicals.

Unless otherwise specified, a haloalkyl radical is understood to be an alkyl radical in which at least one hydrogen is exchanged for a halogen atom, preferably fluorine, chlorine, bromine, particularly preferably fluorine. The haloalkyl radicals can be branched or unbranched and optionally mono- or polysubstituted. Preferred haloalkyl radicals are $CHF_2$, $CH_2F$, $CF_3$, $CH_2$—$CH_2F$, $CH_2$—$CHF_2$, $CH_2CF_3$. ($C_1$-$C_6$) haloalkyl radicals are preferred, with ($C_1$-$C_4$) haloalkyl radicals being particularly preferred and ($C_1$-$C_3$) haloalkyl radicals most particularly preferred, in particular $CHF_2$, $CH_2F$, $CF_3$, $CH_2$—$CH_2F$, $CH_2$—$CHF_2$ and $CH_2CF_3$.

Unless otherwise specified, a haloalkoxy radical is understood to be an alkoxy radical in which at least one hydrogen is exchanged for a halogen atom, preferably fluorine, chlorine, bromine, particularly preferably fluorine. The haloalkoxy radicals can be branched or unbranched and optionally mono- or polysubstituted. Preferred haloalkoxy radicals are $OCHF_2$, $OCH_2F$, $OCF_3$, $OCH_2$—$CFH_2$, $OCH_2$—$CF_2H$, $OCH_2CF_3$. ($C_1$-$C_6$) haloalkoxy radicals are preferred, with ($C_1$-$C_4$) haloalkoxy radicals being particularly preferred and ($C_1$-$C_3$) haloalkoxy radicals most particularly preferred, in particular $OCHF_2$, $OCH_2F$, $OCF_3$, $OCH_2$—$CFH_2$, $OCH_2$—$CF_2H$, $OCH_2CF_3$.

Unless otherwise specified, the term ($C_2$-$C_6$) alkenyl is understood to mean branched and unbranched alkyl groups consisting of 2 to 6 hydrocarbon atoms and having at least one double bond. Examples of ($C_2$-$C_6$) alkenyls are ethenyl (also referred to as vinyl), prop-1-enyl, prop-2-enyl (also referred to as allyl), but-1-enyl, but-2-enyl, but-3-enyl, pent-1-enyl and hex-1-enyl.

The designation ($C_2$-$C_6$) alkenyl includes all possible isomers, i.e. structural isomers (constitutional isomers) and stereoisomers ((Z) and (E) isomers).

Unless otherwise specified, the term carbocycle is understood to mean preferably 3- to 7-membered rings consisting of hydrocarbon groups, which rings can be saturated or unsaturated.

Unless otherwise specified, the term heteroaromatic is understood to mean an aromatic heterocycle which consists of hydrocarbon groups and is preferably 5- to 7-membered and contains one or more heteroatoms, the heteroatoms being selected from the group comprising nitrogen, oxygen and sulfur, preferably nitrogen and/or oxygen. Examples of heteroaromatics are furan, thiophene, pyridine, pyrimidine, thiazole, oxazole, isoxazole, pyridazine, pyrazine, indole, indazole, quinoline, isoquino line, phthalazine and quinazo line.

Owing to their excellent pharmacological activity, the compounds according to the invention of the general structure of formula (I), (I') and of a substructure of formula (I-A), (I-B), (I-C), (I-D), (I-E) or (I-F) derived from formula (I) are suitable for the treatment of various diseases or conditions in which inhibition of the PDE4 enzyme is advantageous.

Such conditions and diseases are inter alia
inflammatory diseases of the joints, in particular rheumatoid arthritis, psoriatic arthritis, ankylosing spondylitis (Bechterew's disease), gout, osteoarthritis;
inflammatory diseases of the skin, in particular psoriasis, atopic dermatitis, lichen planus;
inflammatory diseases of the eyes, in particular uveitis;
gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps;
inflammatory diseases of the internal organs, in particular SLE (systemic lupus erythematosus) including lupus nephritis, chronic prostatitis, interstitial cystitis;
hyperplastic diseases, in particular benign prostatic hyperplasia;
respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia;
diseases of the fibrotic spectrum, in particular hepatic fibrosis, systemic sclerosis, scleroderma;
cancers, in particular haematopoietic cancers, inter alia B-cell lymphoma, T-cell lymphoma, in particular CLL and CML (chronic lymphatic and chronic myeloid leukaemia), ALL and AML (acute lymphatic and acute myeloid leukaemia), and gliomas;
metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension);
psychological disorders, in particular schizophrenia, depression, in particular bipolar or manic depression, dementia, memory loss, generalised anxiety disorder (GAD); and
diseases of the peripheral or central nervous system, in particular Parkinson's disease, multiple sclerosis, Alzheimer's disease, stroke, ALS (amyotrophic lateral sclerosis).

One of the advantages of the compounds according to the invention of the general structure of formula (I), (I') and of a substructure of formula (I-A), (I-B), (I-C), (I-D), (I-E) or (I-F) derived from formula (I) is that they are selective PDE4B inhibitors. The advantage of this selectivity lies in the fact that the PDE4D enzyme for example is not inhibited or is only partly inhibited, and hence the use of such selective PDE4B inhibitors gives rise to no side-effects or to markedly reduced side-effects. Undesired side-effects are for example emesis and nausea, in particular indisposition, vomiting and sickness. The therapeutic range of the compounds according to the invention is therefore advantageous.

The invention therefore also provides a pharmaceutical composition (medicament) containing at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio.

The invention therefore also provides a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament, in particular for the treatment of conditions or diseases that can be treated by inhibition of the PDE4 enzyme, in particular the PDE4B enzyme.

The invention also provides a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints, in particular rheumatoid arthritis, psoriatic arthritis, ankylosing spondylitis (Bechterew's disease), gout, osteoarthritis; and/or inflammatory diseases of the skin, in particular psoriasis, atopic dermatitis, lichen planus; and/or inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; and/or hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

The invention also provides a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints (in particular rheumatoid arthritis, psoriatic arthritis, ankylosing spondylitis (Bechterew's disease), gout, osteoarthritis), the skin (in particular psoriasis, atopic dermatitis, lichen planus) or the eyes (in particular uveitis), of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; of metabolic diseases, in particular type 2 diabetes, metabolic syndrome, obesity/adiposity, fatty liver disease (not alcohol-induced), and/or cardiovascular diseases, in particular arteriosclerosis and PAH (pulmonary arterial hypertension).

The invention also provides a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of rheumatoid arthritis, psoriatic arthritis, ankylosing spondylitis (Bechterew's disease), psoriasis, COPD (chronic obstructive pulmonary disease), asthma, type 2 diabetes and/or metabolic syndrome.

The invention also provides the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the joints, in particular rheumatoid arthritis, psoriatic arthritis, ankylosing spondylitis (Bechterew's disease), gout, osteoarthritis; inflammatory diseases of the skin, in particular psoriasis, atopic dermatitis, lichen planus; inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the joints (in particular rheumatoid arthritis, psoriatic arthritis, ankylosing spondylitis (Bechterew's disease), gout, osteoarthritis), skin (in particular psoriasis, atopic dermatitis, lichen planus) or eyes (in particular uveitis).

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps.

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the internal organs, in particular SLE (systemic lupus erythematosus) including lupus nephritis, chronic prostatitis, interstitial cystitis.

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of hyperplastic diseases, in particular benign prostatic hyperplasia.

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis and pneumonia.

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases of the fibrotic spectrum, in particular hepatic fibrosis, systemic sclerosis and scleroderma.

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas.

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension).

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of psychological disorders, in particular schizophrenia, depression, in particular bipolar or manic depression, dementia, memory loss and generalised anxiety disorder (GAD).

Preferred according to the invention is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases of the peripheral or central nervous system, in particular Parkinson's disease, multiple sclerosis, Alzheimer's disease, stroke and ALS (amyotrophic lateral sclerosis).

Particularly preferred is the use of a compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of one or more of the following diseases or conditions: rheumatoid arthritis, psoriatic arthritis, ankylosing spondylitis (Bechterew's disease), psoriasis, COPD (chronic obstructive pulmonary disease) and asthma.

The invention also provides a method for the treatment of inflammatory diseases of the joints, in particular rheumatoid arthritis, psoriatic arthritis, ankylosing spondylitis (Bechterew's disease), gout, osteoarthritis; inflammatory diseases of the skin, in particular psoriasis, atopic dermatitis, lichen planus; inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis) in a human, which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of inflammatory diseases of the joints (in particular rheumatoid arthritis, psoriatic arthritis, ankylosing spondylitis (Bechterew's disease), gout, osteoarthritis), skin (in particular psoriasis, atopic dermatitis, lichen planus) or eyes (in particular uveitis) in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps, in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of inflammatory diseases of the internal organs, in particular SLE (systemic lupus erythematosus) including lupus nephritis, chronic prostatitis and/or interstitial cystitis, in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of hyperplastic diseases, in particular benign prostatic hyperplasia, in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis and/or pneumonia, in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of diseases of the fibrotic spectrum, in particular hepatic fibrosis, systemic sclerosis and/or scleroderma, in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas, in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension), in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of psychological disorders, in particular schizophrenia, depression, in particular bipolar or manic depression, dementia, memory loss and/or generalised anxiety disorder (GAD), in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of diseases of the peripheral or central nervous system, in particular Parkinson's disease, multiple sclerosis, Alzheimer's disease, stroke and/or ALS (amyotrophic lateral sclerosis), in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of one or more of the following diseases or conditions: rheumatoid arthritis, psoriatic arthritis, ankylosing spondylitis (Bechterew's disease), psoriasis, COPD (chronic obstructive pulmonary disease), asthma and also type 2 diabetes and metabolic syndrome in a human is preferred which is characterised in that a therapeutically effective amount of at least one compound according to the invention of the general structure of formula (I), (I') and of a substructure of formula (I-A), (I-B), (I-C), (I-D), (I-E) or (I-F) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

The amount of active ingredient to be administered to the person or patient varies and is dependent on the patient's weight, age and medical history and on the type of administration, the indication and the severity of the illness. Conventionally 0.1 to 5000 mg/kg, in particular 1 to 500 mg/kg, preferably 2 to 250 mg/kg of body weight of at least one compound according to the invention of the general structure of formula (I), (I') and of a substructure of formula (I-A), (I-B), (I-C), (I-D), (I-E) or (I-F) derived from formula (I) are administered.

The invention relates further to a method (01) for producing a compound according to the invention of general formula (I) in which Q denotes Q1 and $R^1$=H (if n=1 then the target compound corresponds to a compound of formula (I-C) with $R^1$=H and if n=2 then the target compound corresponds to a compound of formula (I-D) with $R^1$=H), encompassing the following steps:

Step (i): Reacting an amidine compound of general formula (II) with a β-keto ester of general formula (III) to form a 4-hydroxypyrimidine compound of formula (IV)

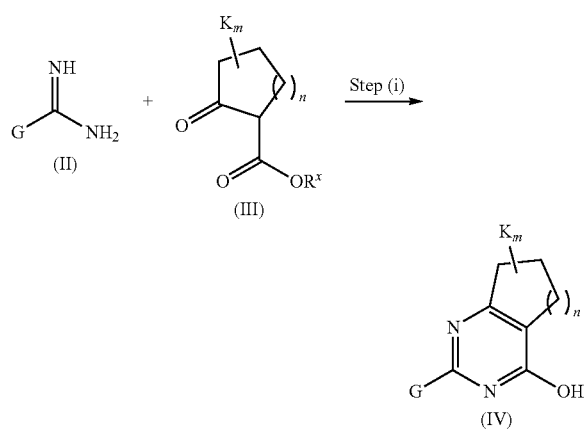

in a solvent such as for example ethanol or dimethylformamide and in the presence of a base (e.g. sodium ethanolate, triethylamine or caesium carbonate) at a temperature in the range from approximately 50° C. to approximately 130° C.;

Step (ii): Chlorination of the 4-hydroxypyrimidine compound of formula (IV) with a chlorinating agent to form a compound (V)

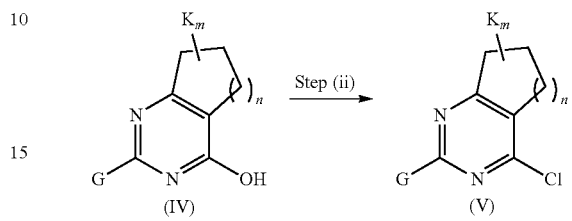

in a solvent, wherein the chlorinating agent can be phosphorus oxychloride;

Step (iii): Reacting the 4-chloropyrimidine compound of formula (V) with an aniline of formula (VI) to form a compound of formula (VII)

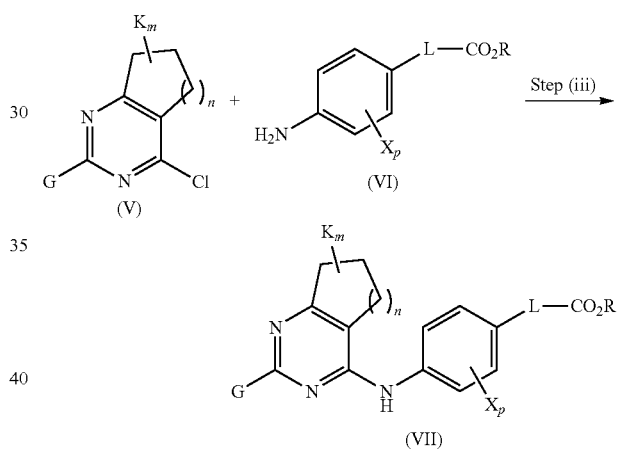

in a solvent and optionally in the presence of a base, acid or transition metal catalyst;

Step (iv): Acid or basic ester cleavage of the compound of formula (VII) to form the target compound of formula (I) in an organic solvent, which can contain water.

Step (i) of method (01), namely the reaction of an amidine compound of general formula (II) with a β-keto ester of general formula (III) to form a 4-hydroxypyrimidine compound of formula (IV), is a condensation reaction. The β-keto ester of general formula (III) can also be present in the tautomeric enol form. Condensation reactions are generally known (see for example Chemistry—A European Journal 2008, 14, 6836-6844). For example, the compounds of general formula (II) and general formula (III) can be reacted in the presence of a base such as triethylamine or sodium ethylate in ethanol as solvent at a temperature in the range from approximately 70° C. to approximately 90° C. to form a compound of general formula (IV).

Step (ii) of method (01) is a chlorination of the hydroxyl group of the 4-hydroxypyrimidine of general formula (IV) by standard methods (see for example Journal of the Chemical Society 1951, 1218-1221; Bioorganic & Medicinal Chemistry 2010, 18, 2704-2712). For example, compounds of general formula (V) can be produced by reacting 4-hydroxypyrimidines of general formula (IV) with phosphorus oxychloride at a temperature in the range from approximately 20° C. to approximately 100° C., preferably at a temperature from approximately 50° C. to approximately 100° C.

Step (iii) of method (01), namely the reaction of the 4-chloropyrimidine compounds of general formula (V) with the corresponding anilines of general formula (VI) to form the compounds of general formula (VII) takes place by standard methods of nucleophilic aromatic substitution in a solvent and optionally in the presence of a base. Suitable solvents are known to the person skilled in the art. Examples of such solvents are dioxane, tetrahydrofuran, dimethylformamide or dimethylsulfoxide. Examples of suitable bases are 1,8-diazabicyclo[5.4.0]undec-7-ene (DBU), triethylamine, sodium hydroxide solution and caesium or potassium carbonate. The reaction can take place at a temperature in the range from approximately 20° C. to approximately 200° C. The reaction preferably takes place at a temperature in the range from 50° C. to 200° C. Alternatively, the compounds of general formula (VII) can also be obtained by reacting compounds of general formula (V) and general formula (VI) in the presence of an acid, such as for example hydrochloric acid, and dimethylformamide as the solvent or under the conditions for palladium-catalysed cross-coupling reactions, as described in method (02).

The ester cleavage (ester hydrolysis) in step (iv) of method (01) takes place by known methods. Ester cleavages are described for example by P. G. M. Wuts, T. W. Greene in Greene's Protective Groups in Organic Synthesis, 4th Edition, 2007, pages 538-616, Wiley-Interscience. They can be performed hydrolytically, for example, in the presence of acids or bases (e.g. alkali hydroxides such as for example lithium or sodium hydroxide) in an organic solvent to which varying proportions of water can be added. Other frequently used methods of ester cleavage involve the acid-catalysed cleavage of a tert-butyl ester (R=tert-butyl) by generally known methods, for example using trifluoroacetic acid in dichloromethane, or the hydrogenolysis of benzyl esters.

The invention relates likewise to a method (02) for preparing a compound according to the invention of general formula (I) in which Q denotes Q1 and $R^1$ denotes hydrogen (if n=1 then the target compound corresponds to a compound of formula (I-C) with $R^1$=H and if n=2 then the target compound corresponds to a compound of formula (I-D) with $R^1$=H), encompassing the following steps:

Step (i'): Reacting a compound of formula (VIII) with a compound of formula (VI) to form a compound of formula (IX)

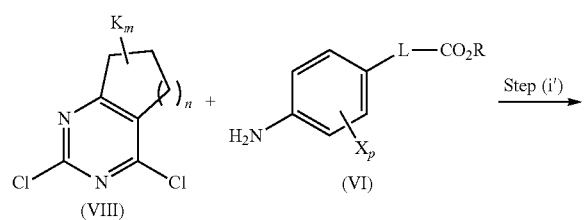
(VIII) (VI)

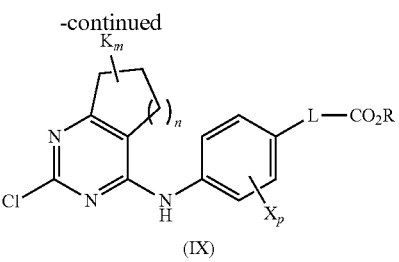
(IX)

in a solvent (e.g. dioxane, tetrahydrofuran, dimethylformamide, N-methyl pyrrolidone or dimethylsulfoxide) and optionally in the presence of a base (e.g. 1,8-diazabicyclo[5.4.0]undec-7-ene (DBU), triethylamine, sodium hydroxide solution, caesium or potassium carbonate) at a temperature in the range from approximately 20° C. to approximately 200° C., preferably from approximately 50° C. to approximately 130° C.;

Step (ii'): Reacting the compound of formula (IX) with a compound G-M to form a compound of formula (VII) under the conditions of a Suzuki coupling or a Stille coupling

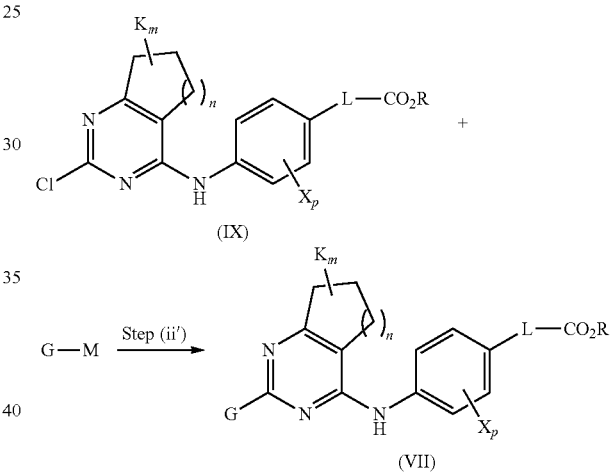

wherein G in the compound G-M has the meaning described in connection with the compounds according to the invention and M has the following meaning:

In the case of a Suzuki coupling M denotes $B(OH)_2$ (boronic acid), $B(OR^X)_2$ (boronic acid ester) or an optionally ($C_1$-$C_6$) alkyl-substituted 1,3,2-dioxaborolane (e.g. 4,4,5,5-tetramethyl-1,3,2-dioxaborolane; pinacol boronic acid ester) and in the case of a Stille coupling M denotes $SnR^x_3$ (e.g. $M=Sn(CH_3)_3$, $SnBn_3$, trimethylstannyl or tributylstannyl compounds);

Step (iii'): Acid or basic ester cleavage of the compound of formula (VII) to form the target compound of formula (I)Iby the method described in method (01) for step (iv).

Step (i') of method (02), namely the reaction of 2,4-dichloropyrimidine compounds of general formula (VIII) with suitable anilines (VI) to produce compounds of formula (IX), takes place by known methods of nucleophilic aromatic substitutions. The reaction can be performed for example in a solvent such as dioxane, tetrahydrofuran, dimethylformamide, N-methyl pyrrolidone or dimethylsulfoxide with or without addition of a base such as 1,8-diazabicyclo[5.4.0]undec-7-ene (DBU), triethylamine, sodium hydroxide solution, caesium or potassium carbonate at a temperature in the range from approximately 20° C. to approximately 200° C., preferably from approximately 50° C. to approximately 130° C.

Step (ii') of method (02), namely the reaction under Stille or Suzuki coupling reaction conditions, takes place by known methods (cf. Tetrahedron 2005, 61, 2245-67). The Suzuki coupling can be performed for example in the presence of a catalyst such as tetrakis(triphenylphosphine)palladium(0) or [1,1'-bis(diphenylphosphino)ferrocene]dichloropalladium(II) complex and a base (e.g. caesium carbonate) in a solvent or solvent blend (e.g. dioxane or acetonitrile/water blend).

Unless otherwise specified, the radicals R and $R^x$ in the general formulae of the compounds that are used or reacted in the aforementioned methods (01) and (02) are defined as follows:

R denotes a leaving group (e.g. methyl, ethyl, tert-butyl or benzyl) and $R^x$ denotes ($C_1$-$C_6$) alkyl, preferably methyl and butyl.

All other chemical groupings, substituents and indices have the meanings given in relation to the compound of formula (I).

The compounds according to the invention are specified in the table below, without limiting the invention thereto.

TABLE 1

(I')

| No. | Z | k | n | m | $R^1$ | Q | p | L |
|---|---|---|---|---|---|---|---|---|
| 1 | 3-Br | 1 | 1 | 0 | H | Q1 | 0 | CH2 |
| 2 | 2-F, 3-F | 2 | 1 | 0 | H | Q1 | 0 | CH2 |
| 3 | 2-F, 3-OMe | 2 | 1 | 0 | H | Q1 | 0 | CH2 |
| 4 | 2-Cl, 3-OMe | 2 | 1 | 0 | H | Q1 | 0 | CH2 |
| 5 | 3-OCHF2 | 1 | 1 | 0 | H | Q1 | 0 | CH2 |
| 6 | 3-OCF3 | 1 | 1 | 0 | H | Q1 | 0 | CH2 |
| 7[a] | 3-OEt | 1 | 1 | 0 | H | Q1 | 0 | CH2 |
| 8[b] | 3-OMe | 1 | 1 | 0 | H | Q1 | 0 | CH2 |
| 9[b] | 3-Cl | 1 | 1 | 0 | H | Q1 | 0 | CH2 |
| 10 | 2-Cl | 1 | 1 | 0 | H | Q1 | 0 | CH2 |
| 11 | 2-Cl | 1 | 1 | 0 | H | Q1 | 0 | Bd |
| 12 | 2-Cl | 1 | 2 | 0 | H | Q1 | 0 | CH2 |
| 13 | 2-F, 3-OMe | 2 | 1 | 0 | H | Q1 | 0 | Bd |
| 14 | 2-Cl, 3-OMe | 2 | 1 | 0 | H | Q1 | 0 | Bd |
| 15 | 2-F, 3-F | 2 | 1 | 0 | H | Q1 | 0 | Bd |
| 16 | — | 0 | 1 | 0 | H | Q1 | 0 | CH2 |
| 17 | 2-F | 1 | 1 | 0 | H | Q1 | 0 | CH2 |
| 18 | 2-Br | 1 | 1 | 0 | H | Q1 | 0 | CH2 |
| 19[a] | 2-Cl | 1 | 2 | 0 | H | Q1 | 0 | Bd |
| 20 | 2-OMe | 1 | 1 | 0 | H | Q1 | 0 | CH2 |
| 21 | 2-CF3 | 1 | 1 | 0 | H | Q1 | 0 | CH2 |
| 22 | 2-CN | 1 | 1 | 0 | H | Q1 | 0 | CH2 |
| 23 | 2-Me | 1 | 1 | 0 | H | Q1 | 0 | CH2 |

[a] present as a hydrochloride addition salt;
[b] present as a trifluoroacetic acid addition salt.

TABLE 2

(I")

| No. | G | Z | k | n | m | $R^1$ | L | $R^2$ |
|---|---|---|---|---|---|---|---|---|
| 2-1 | G10 | — | 0 | 1 | 0 | H | CH2 | H |
| 2-2[b] | G11 | — | 0 | 1 | 0 | H | CH2 | H |
| 2-3[b] | G12 | — | 0 | 1 | 0 | H | CH2 | H |
| 2-4[b] | G4 | — | 0 | 1 | 0 | H | CH2 | H |
| 2-5 | G13 | — | 0 | 1 | 0 | H | CH2 | H |
| 2-6 | G1 | 2-Cl | 1 | 1 | 0 | H | CH2 | Me |

[b] present as a trifluoroacetic acid addition

TABLE 3

(I''')

| No. | G | Z | k | n | m | $R^1$ | L | $R^2$ |
|---|---|---|---|---|---|---|---|---|
| 3-1 | G1 | 2-Cl | 1 | 1 | 0 | H | Bd | H |
| 3-2 | G1 | 2-Cl | 1 | 2 | 0 | H | CH2 | H |
| 3-3 | G1 | 2-Cl | 1 | 2 | 0 | H | Bd | H |
| 3-4 | G1 | 2-Cl | 1 | 2 | 0 | H | CH2 | Me |

In before tables Me denotes methyl, Et denotes ethyl and Bd denotes bond.

The compounds according to the invention can be produced in the manner described below.

The following abbreviations are used hereafter:
eq.=equivalent; APCI=atmospheric pressure chemical ionization; BINAP=2,2'-bis(diphenylphosphino)-1,1'-binaphthyl; calc.=calculated; BOP=(benzotriazol-1-yloxy)tris(dimethylamino)phosphonium hexafluorophosphate; DMAP=N,N-dimethylpyridin-4-amine; DMF=N,N-dimethylformamide; DMSO=dimethylsulfoxide; ES-MS=electrospray mass spectrometry; NMP=N-methyl-2-pyrrolidone; fd.=found; h=hour; min=minutes; $R_t$=retention time; tert=tertiary; THF=tetrahydrofuran; TOFMS=time-of-flight mass spectrometer Unless otherwise specified, the following analytical HPLC methods were used:
Method 1:
Column: Agilent Zorbax Extend, 1.8 μm, 4.6×30 mm
Detection: 254 nm (or 215 nm)
Solvent A: Water/0.1% formic acid
Solvent B: Acetonitrile/0.1% formic acid
Gradient:

| Time in min | % A | % B | Flow rate in ml/min |
|---|---|---|---|
| 0.0 | 95.0 | 5.0 | 2.5 |
| 3.0 | 5.0 | 95.0 | 2.5 |

-continued

| Time in min | % A | % B | Flow rate in ml/min |
|---|---|---|---|
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 2:
Column: Ascentis Express C18, 2.7 µm, 3 cm×2.1 mm
Column temperature: 30° C.
Injection volume: 1 µl
System dead time: 0.2 min
Detection: MM-ES+APCI+DAD (254 nm)
Solvent A: Water/0.1% formic acid
Solvent B: Methanol/0.1% formic acid
Gradient:

| Time in min | % A | % B | Flow rate in ml/min |
|---|---|---|---|
| 1.0 | 95 | 5 | 0.8 |
| 4.0 | 0 | 100 | 0.8 |
| 5.0 | 0 | 100 | 0.8 |
| 6.0 | 95 | 5 | 0.8 |
| 6.5 | 95 | 5 | 0.8 |

Method 3:
Hardware: Coupled Agilent 1290 Infinity UHPLC-TOF system
Column: Agilent Zorbax SB-C18, Rapid Resolution HD, 1.8 µm
Detection: Agilent 6224 time-of-flight mass spectrometer
Ion source: Dual ESI
Solvent A: Water/0.1% formic acid
Solvent B: Acetonitrile/0.1% formic acid
UV: 190-400 nm
Column temperature: 80° C.
Gradient:

| Time in min | % A | % B | Flow rate in ml/min |
|---|---|---|---|
| 0.0 | 98 | 2 | 2.3 |
| 1.0 | 0 | 100 | 2.3 |
| 1.09 | 0 | 100 | 2.3 |
| 1.11 | 98 | 2 | 2.3 |
| 1.3 | 98 | 2 | 2.3 |

General Procedure No. 1 (GP1):
2M sodium carbonate solution (0.53 ml, 5.0 eq.) and tetrakis(triphenylphosphine)palladium(0) (8.0 mg, 0.03 eq.) were added successively to a solution of tert-butyl 2-(4-(tert-butoxycarbonyl(2-chloro-6,7-dihydro-5H-cyclopenta[d]pyrimidin-4-yl)amino)phenyl)acetate (0.217 mmol, 1.0 eq.) and boronic acid (0.326 mmol, 1.5 eq.) in 1,2-dimethoxyethane (4.4 ml) and the mixture was heated to 120° C. in a microwave for 1 h under an argon atmosphere. The reaction mixture was cooled and boronic acid (0.326 mmol, 1.5 eq.) and tetrakis(triphenylphosphine)palladium(0) (8.0 mg, 0.03 eq.) were again added. The mixture was then heated to 120° C. in the microwave for a further hour. After cooling to room temperature the reaction was ended by adding water (5 ml). The product was extracted with dichloromethane (3×8 ml), dried with sodium sulfate, filtered and freed from solvent under reduced pressure. The crude product was purified by column chromatography.

General Procedure No. 2 (GP2):
The product obtained by GP1 (1 eq.) was mixed with trifluoroacetic acid (50 eq.) and stirred for 30 min at room temperature. The acid was then distilled off under reduced pressure and the product obtained was dried under high vacuum.

EXAMPLE 1

2-(4-(2-(3,4-Difluorophenyl)-6,7-dihydro-5H-cyclopenta[d]pyrimidin-4-ylamino)phenyl)acetic acid (compound no. 2)

1a) tert-Butyl 2-(4-(2-chloro-6,7-dihydro-5H-cyclopenta[d]pyrimidin-4-ylamino)phenyl)acetate 2,4-Dichloro-6,7-dihydro-5H-cyclopenta[d]pyrimidine (21.60 g, 114 mmol), tert-butyl 2-(4-aminophenyl)acetate (24.87 g, 120 mmol) and diisopropylethylamine (39.8 ml, 229 mmol) in NMP (570 ml) were stirred overnight at 80° C. After cooling, the mixture was diluted with ethyl acetate and washed with water. The organic phase was then dried with magnesium sulfate and concentrated to small volume under reduced pressure. The residue was chromatographed [silica gel, hexane with 0-90% ethyl acetate] and the crude product thus obtained was crystallised out in hexane/ethyl acetate. Yellow solid. Yield: 8.5 g (21% of theoretical).

1b) tert-Butyl 2-(4-(tert-butoxycarbonyl(2-chloro-6,7-dihydro-5H-cyclopenta[d]pyrimidin-4-yl)amino)phenyl)acetate DMAP (373 mg, 3.1 mmol) was added to a solution of tert-butyl 2-(4-(2-chloro-6,7-dihydro-5H-cyclopenta[d]pyrimidin-4-ylamino)phenyl)acetate (11.0 g, 30.6 mmol) and di-tert-butyl-dicarbonate (7.45 ml, 32.1 mmol) in THF (200 ml) and the mixture was stirred for 6 h at room temperature. Then the solvent was distilled off and the residue was stirred in dichloromethane/hexane. The solid was filtered off, washed with dichloromethane/hexane and dried. White solid. Yield: 10.5 g (75% of theoretical).
LC-MS (method 1): $R_t$=2.95 min, m/z: $[M+H]^+$=460

1c) 2-(4-(tert-Butoxycarbonyl(2-(3,4-difluorophenyl)-6,7-dihydro-5H-cyclopenta[d]pyrimidin-4-yl)amino)phenyl)acetic acid tert-butyl ester 3,4-Difluorophenyl boronic acid (77 mg, 0.489 mmol), 2M sodium carbonate solution (0.8 ml) and tetrakis(triphenylphosphine)palladium(0) (11 mg, 0.010 mmol) were added successively under protective gas to a solution of tert-butyl 2-(4-(tert-butoxycarbonyl(2-chloro-6,7-dihydro-5H-cyclopenta[d]pyrimidin-4-yl)amino)phenyl)acetate (150 mg, 0.326 mmol) in ethylene glycol dimethyl ether (7 ml). Then the mixture was heated to 120° C. for 1 h in a microwave. The mixture was processed by adding water (8 ml) and extracting with dichloromethane. The organic phases were dried with magnesium sulfate and concentrated to small volume. The residue was purified by column chromatography [silica gel 60; hexane/ethyl acetate 9:1]. Yield: 150 mg (86% of theoretical).
LC-MS (method 3): $R_t$=1.12 min, m/z: $[M+H]^+$=538.3

1d) 2-(4-(2-(3,4-Difluorophenyl)-6,7-dihydro-5H-cyclopenta[d]pyrimidin-4-ylamino)phenyl)acetic acid Trifluoroacetic acid (0.5 ml) was added to a solution of the ester from 1c) (190 mg, 0.353 mmol) in dichloromethane (2.3 ml) and the mixture was stirred overnight at room temperature. Then the solvent was distilled off and the residue was mixed with water (10 ml) and 2M sodium carbonate solution (2 ml). After stirring for 15 min, the pH was adjusted to 2 with 2N aqueous hydrochloric acid and extraction was performed with dichloromethane/methanol (9:1). The combined organic phases were washed with sodium chloride solution, dried with magnesium sulfate and concentrated to small volume. The residue was stirred with diethyl ether (10 ml) and ethanol (0.5 ml), filtered, rewashed with a little ether and dried. White solid. Yield: 93 mg (69% of theoretical).

LC-MS (method 3): $R_t$=0.67 min, m/z: $[M+H]^+$=382.1

EXAMPLE 2

2-(4-(2-(3-Fluoro-4-methoxyphenyl)-6,7-dihydro-5H-cyclopenta[d]pyrimidin-4-ylamino)phenyl)acetic acid (compound no. 3)

2a) 2-(4-(tert-Butoxycarbonyl(2-(3-fluoro-4-methoxyphenyl)-6,7-dihydro-5H-cyclopenta[d]pyrimidin-4-yl)amino)phenyl)acetic acid tert-butyl ester tert-Butyl-2-(4-(tert-butoxycarbonyl(2-chloro-6,7-dihydro-5H-cyclopenta[d]pyrimidin-4-yl)amino)phenyl)acetate (150 mg, 0.326 mmol) and 3-fluoro-4-methoxyphenyl boronic acid (83 mg, 0.489 mmol) were reacted in an analogous manner to procedure 1c). Yield: 150 mg (84% of theoretical).

LC-MS (method 3): $R_t$=1.09 min, m/z: $[M+H]^+$=550.3

2b) 2-(4-(2-(3-Fluoro-4-methoxyphenyl)-6,7-dihydro-5H-cyclopenta[d]pyrimidin-4-ylamino)phenyl)acetic acid The title compound was produced from the ester from 2a) (146 mg, 0.267 mmol) in an analogous manner to procedure 1d). White solid. Yield: 52 mg (50% of theoretical).

LC-MS (method 3): $R_t$=0.55 min, m/z: $[M+H]^+$=394.2

EXAMPLE 3

2-(4-(2-(3-Chloro-4-methoxyphenyl)-6,7-dihydro-5H-cyclopenta[d]pyrimidin-4-ylamino)phenyl)acetic acid (compound no. 4)

3a) 2-(4-(tert-Butoxycarbonyl(2-(3-chloro-4-methoxyphenyl)-6,7-dihydro-5H-cyclopenta[d]pyrimidin-4-yl)amino)phenyl)acetic acid tert-butyl ester Produced in an analogous manner to Example 1c) from tert-butyl 2-(4-(tert-butoxycarbonyl(2-chloro-6,7-dihydro-5H-cyclopenta[d]pyrimidin-4-yl)amino)phenyl)acetate (150 mg, 0.326 mmol) and 3-chloro-4-methoxyphenyl boronic acid (91 mg, 0.489 mmol). White solid. Yield: 140 mg (76% of theoretical).

LC-MS (method 3): $R_t$=1.12 min, m/z: $[M+H]^+$=566.2

3b) 2-(4-(2-(3-Chloro-4-methoxyphenyl)-6,7-dihydro-5H-cyclopenta[d]pyrimidin-4-ylamino)phenyl)acetic acid Produced from the ester from 3a) (140 mg, 0.247 mmol) in an analogous manner to Example 1d). White solid. Yield: 79 mg (78% of theoretical).

LC-MS (method 3): $R_t$=0.59 min, m/z: $[M+H]^+$=410.1

EXAMPLE 4

2-(4-(2-(4-(Difluoromethoxy)phenyl)-6,7-dihydro-5H-cyclopenta[d]pyrimidin-4-ylamino)phenyl)acetic acid (compound no. 5)

4a) 2-(4-(tert-Butoxycarbonyl(2-(4-(difluoromethoxy)phenyl)-6,7-dihydro-5H-cyclopenta[d]pyrimidin-4-yl)amino)phenyl)acetic acid tert-butyl ester Reaction of tert-butyl 2-(4-(tert-butoxycarbonyl(2-chloro-6,7-dihydro-5H-cyclopenta[d]pyrimidin-4-yl)amino)phenyl)acetate (150 mg, 0.326 mmol) and 4-(difluoromethoxy)phenyl boronic acid (91 mg, 0.489 mmol) in an analogous manner to Example 1c). Yield: 140 mg (76% of theoretical).

LC-MS (method 3): $R_t$=1.09 min, m/z: $[M+H]^+$=568.3

4b) 2-(4-(2-(4-(Difluoromethoxy)phenyl)-6,7-dihydro-5H-cyclopenta[d]pyrimidin-4-ylamino)phenyl)acetic acid The ester obtained by procedure 4a) (430 mg, 0.758 mmol) was converted to the title compound in an analogous manner to Example 1d). Light-yellow solid. Yield: 183 mg (59% of theoretical).

LC-MS (method 3): $R_t$=0.57 min, m/z: $[M+H]^+$=412.1

EXAMPLE 5

2-(4-(2-(4-(Trifluoromethoxy)phenyl)-6,7-dihydro-5H-cyclopenta[a]pyrimidin-4-ylamino)phenyl)acetic acid (compound no. 6)

5a) 2-(4-(tert-Butoxycarbonyl(2-(4-(trifluoromethoxy)phenyl)-6,7-dihydro-5H-cyclopenta[d]pyrimidin-4-yl)amino)phenyl)acetic acid tert-butyl ester Produced in an analogous manner to procedure 1c). White solid. Yield: 160 mg (84% of theoretical).

5b) 2-(4-(2-(4-(Trifluoromethoxy)phenyl)-6,7-dihydro-5H-cyclopenta[d]pyrimidin-4-ylamino)phenyl)acetic acid Reaction of the ester from 5a) (150 mg, 0.256 mmol) in an analogous manner to the procedure for Example 1d). White solid. Yield: 93 mg (85% of theoretical).

LC-MS (method 3): $R_t$=0.72 min, m/z: $[M+H]^+$=430.1

EXAMPLE 6

2-(4-(2-(4-Ethoxyphenyl)-6,7-dihydro-5H-cyclopenta[d]pyrimidin-4-ylamino)phenyl)acetic acid (compound no. 7)

6a) 2-(4-(tert-Butoxycarbonyl(2-(4-ethoxyphenyl)-6,7-dihydro-5H-cyclopenta[d]pyrimidin-4-yl)amino)phenyl)acetic acid tert-butyl ester Produced from tert-butyl 2-(4-(tert-butoxycarbonyl(2-chloro-6,7-dihydro-5H-cyclopenta[d]pyrimidin-4-yl)amino)phenyl)acetate (150 mg, 0.326 mmol) and 4-ethoxyphenyl boronic acid (81 mg, 0.489 mmol) in an analogous manner to the procedure for Example 1c). Yield: 110 mg (62% of theoretical).

6b) 2-(4-(2-(4-Ethoxyphenyl)-6,7-dihydro-5H-cyclopenta[d]pyrimidin-4-ylamino)phenyl)acetic acid Produced in an analogous manner to Example 1d) from the ester obtained in 6a) (0.110 mg, 0.202 mmol). Yield: 75 mg (87% of theoretical, hydrochloride).

LC-MS (method 3): $R_t$=0.55 min, m/z: $[M+H]^+$=390.2

EXAMPLE 7

2-(4-(2-(4-Methoxyphenyl)-6,7-dihydro-5H-cyclopenta[d]pyrimidin-4-ylamino)phenyl)acetic acid as 2,2,2-trifluoroacetic acid addition salt (compound no. 8)

tert-Butyl 2-(4-(tert-butoxycarbonyl(2-chloro-6,7-dihydro-5H-cyclopenta[d]pyrimidin-4-yl)amino)phenyl)acetate (100 mg, 0.217 mmol) was reacted with 4-methoxyphenyl boronic acid as described in GP1. The product obtained after purification by column chromatography [silica gel; cyclohexane with 5-10% ethyl acetate] (93 mg; LC-MS (method 3): $R_t$=0.98 min) was deprotected with trifluoroacetic acid (0.766 ml, 8.77 mmol) as described in GP2. Yield: 96 mg.

LC-MS (method 3): $R_t$=0.49 min, m/z: $[M+H]^+$=376.2

EXAMPLE 8

2-(4-(2-(4-Chlorophenol)-6,7-dihydro-5H-cyclopenta[d]pyrimidin-4-ylamino)phenyl)acetic acid as 2,2,2-trifluoroacetic acid addition salt (compound no. 9)

The reaction of tert-butyl 2-(4-(tert-butoxycarbonyl(2-chloro-6,7-dihydro-5H-cyclopenta[d]pyrimidin-4-yl) amino)phenyl)acetate (100 mg, 0.217 mmol) with 4-chlorophenyl boronic acid as described in GP1 yielded after column chromatography [silica gel; cyclohexane with 3-5% ethyl acetate] 72 mg of intermediate (LC-MS (method 3): $R_t$=1.14 min), which was then converted to the target compound by treatment with trifluoroacetic acid (0.519 ml, 6.73 mmol) as described in GP2. Yield: 87 mg.

LC-MS (method 3): $R_t$=0.62 min, m/z: $[M+H]^+$=380.1

EXAMPLE 9

2-(4-(2-(3-Chlorophenyl)-6,7-dihydro-5H-cyclopenta[d]pyrimidin-4-ylamino)phenyl)acetic acid (compound no. 10)

9a) 2-(3-Chlorophenyl)-6,7-dihydro-5H-cyclopenta[d]pyrimidin-4-ol

3-Chlorobenzimidamide hydrochloride (1.00 g, 5.23 mmol) and triethylamine (0.73 ml, 5.23 mmol) were added to a solution of 2-oxocyclopentanecarboxylic acid methyl ester (0.744 g, 5.23 mmol) in ethanol (5.2 ml) and the mixture was stirred at 80° C. for 4 h. Then the reaction mixture was allowed to cool to room temperature. The precipitate was filtered off, washed with ethanol and dried under vacuum. White solid. Yield: 436 mg (34% of theoretical).

LC-MS (method 1): $R_t$=1.76 min, m/z: $[M+H]^+$=247.1/249.2, $[M+H]^-$=245.3/247.1

9b) 4-Chloro-2-(3-chlorophenyl)-6,7-dihydro-5H-cyclopenta[d]pyrimidine 2-(3-Chlorophenyl)-6,7-dihydro-5H-cyclopenta[d]pyrimidin-4-ol (100 mg, 0.41 mmol) and phosphorus oxychloride (1.62 ml, 17.38 mmol) were heated to 90° C., causing the initial suspension to change into a solution. After 1 h the reaction mixture was cooled to room temperature and water (20 ml) was added dropwise. The temperature was held at 40° C. by cooling with ice. Then the solution was made alkaline with sodium hydrogen carbonate solution and then extracted with dichloromethane. The organic phases were dried with magnesium sulfate and freed from solvent. White solid. Yield: 86 mg (80% of theoretical).

LC-MS (method 1): $R_t$=3.10 min, m/z: $[M+H]^+$=265.1/267.2

9c) 2-(4-(2-(3-Chlorophenyl)-6,7-dihydro-5H-cyclopenta[d]pyrimidin-4-ylamino)phenyl)acetic acid 2 drops of concentrated hydrochloric acid were added to 4-chloro-2-(3-chlorophenyl)-6,7-dihydro-5H-cyclopenta[d] pyrimidine (84 mg, 0.317 mmol) and 2-(4-aminophenyl) acetic acid (48 mg, 0.317 mmol) in DMF and the mixture was stirred overnight at 100° C. The reaction mixture was concentrated to small volume under vacuum and the residue purified by chromatography [silica gel, hexane/ethyl acetate 0-100%]. The product thus obtained was then dried in a vacuum oven to remove solvent residues. Yield: 36 mg (30% of theoretical).

LC-MS (method 1): $R_t$=1.89 min, m/z: $[M+H]^+$=380.3/382.4, $[M+H]^-$=378.2/380.3

EXAMPLE 10

4-(2-(3-Chlorophenyl)-6,7-dihydro-5H-cyclopenta[d]pyrimidin-4-ylamino)benzoic acid (compound no. 11)

10a) 4-(2-(3-Chlorophenyl)-6,7-dihydro-5H-cyclopenta[d]pyrimidin-4-ylamino)benzoic acid methyl ester A solution of 4-chloro-2-(3-chlorophenyl)-6,7-dihydro-5H-cyclopenta[d]pyrimidine (100 mg, 0.377 mmol), 4-aminobenzoic acid methyl ester (57 mg, 0.377 mmol), caesium carbonate (184 mg, 0.566 mmol) and BINAP (18 mg, 0.028 mmol) in dioxane (2.5 ml) was flushed with nitrogen, then mixed with palladium(II) acetate (4 mg, 0.19 mmol) and then heated for 2 h to 90° C. under a nitrogen atmosphere. After cooling to room temperature the solid was filtered off and washed with dioxane. The filtrate was concentrated to small volume and the residue purified by column chromatography [silica gel, hexane/ethyl acetate 0-100%]. White solid. Yield: 90 mg (63% of theoretical).

LC-MS (method 1): $R_t$=2.77 min, m/z: $[M+H]^+$=380.3/382.1, $[M+H]^-$=378.2/380.0

10b) 4-(2-(3-Chlorophenyl)-6,7-dihydro-5H-cyclopenta[d]pyrimidin-4-ylamino)benzoic acid The product from procedure 10a) (86 mg, 226 mmol) in THF (2 ml) was mixed with lithium hydroxide (22 mg, 0.906 mmol) and stirred at room temperature for 18 h. Then the solvent was distilled off under vacuum and the residue acidified and purified by means of solid phase extraction (SAX cartridge). Yield: 75 mg (91% of theoretical).

LC-MS (method 1): $R_f$=2.18 min, m/z: $[M+H]^+$=366, $[M+H]^-$=364

EXAMPLE 11

2-(4-(2-(3-Chlorophenyl)-5,6,7,8-tetrahydroquinazolin-4-ylamino)phenyl)acetic acid (compound no. 12)

11a) 2-(3-Chlorophenyl)-5,6,7,8-tetrahydroquinazolin-4-ol

Sodium ethylate solution (21 wt. %, 43.9 ml, 118 mmol) was added to 3-chlorobenzimidamide hydrochloride (5.61 g, 29.4 mmol) and 2-oxocyclohexanecarboxylic acid ethyl ester (4.70 ml, 29.4 mmol) in ethanol (100 ml) at 0° C. and the mixture was then stirred overnight at 90° C. The solvent was distilled off and the residue diluted with iced water and filtered. The filter cake was washed with water and then dried in a vacuum oven. Beige solid. Yield: 4.97 g (62% of theoretical).

LC-MS (method 1): $R_f$=1.93 min, m/z: $[M+H]^+$=261.1/263.1, $[M+H]^-$=259.1/261.0

11b) 4-Chloro-2-(3-chlorophenyl)-5,6,7,8-tetrahydroquinazoline 2-(3-Chlorophenyl)-5,6,7,8-tetrahydroquinazolin-4-ol (1.00 g, 3.84 mmol) and phosphorus oxychloride (4.0 ml, 42.9 mmol) were heated to 90° C. for 30 min. Then the reflux condenser was removed and the reaction mixture was stirred overnight at room temperature. Iced water was added, the mixture was neutralised with saturated sodium hydrogen carbonate solution and extraction was performed with dichloromethane. The organic phases were dried with magnesium sulfate and concentrated to small volume under vacuum. Light-yellow solid. Yield: 0.96 g (90% of theoretical).

LC-MS (method 1): $R_f$=3.21 min, m/z: $[M]^+$=279.1/281.3

11c) 2-(4-(2-(3-Chlorophenyl)-5,6,7,8-tetrahydroquinazolin-4-ylamino)phenyl)acetic acid ethyl ester Produced from 4-chloro-2-(3-chlorophenyl)-5,6,7,8-tetrahydroquinazoline (715 mg, 2.56 mmol) and (4-aminophenyl)acetic acid ethyl ester (482 mg, 2.69 mmol) in an analogous manner to procedure 10a). Yellow solid. Yield: 908 mg (84% of theoretical)

LC-MS (method 1): $R_f$=2.24 min, m/z: $[M+H]^+$=422.2/424.2, $[M+H]^-$=420.2/422.1

11d) 2-(4-(2-(3-Chlorophenyl)-5,6,7,8-tetrahydroquinazolin-4-ylamino)phenyl)acetic acid The ethyl ester from 11c) was converted to the free acid by stirring with lithium hydroxide in a THF/water mixture at room temperature. Beige solid.

LC-MS (method 1): $R_f$=1.70 min, m/z: $[M+H]^+$=394.2/396.2, $[M+H]^-$=392.0/394.1

EXAMPLE 12

4-(2-(3-Fluoro-4-Methoxyphenyl)-6,7-Dihydro-5H-Cyclopenta[d]pyrimidin-4-ylamino)benzoic acid (compound no. 13)

12a) 4-(2-Chloro-6,7-dihydro-5H-cyclopenta[d]pyrimidin-4-ylamino)benzoic acid ethyl ester Caesium carbonate (6.20 g, 19.04 mmol), BINAP (592 mg, 0.95 mmol) and palladium(II) acetate (178 mg, 0.79 mmol) were added under a protective gas atmosphere to a solution of 2,4-dichloro-6,7-dihydro-5H-cyclopenta[d]pyrimidine (3.00 g, 15.87 mmol) and 4-aminobenzoic acid ethyl ester (2.62 g, 15.87 mmol) in anhydrous 1,4-dioxane (60 ml) and the mixture was stirred at 100° C. for 2 h. Then the reaction mixture was poured onto a silica gel column and eluted with dichloromethane. White solid. Yield: 978 mg (19% of theoretical)

LC-MS (method 2): $R_f$=3.85 min, m/z: $[M+H]^+$=318.2
13C-NMR (101 MHz, DMSO-d6, δ ppm): 14.2, 21.1, 27.8, 34.3, 60.2, 117.7, 122.3, 123.8, 130.1, 144.6, 155.1, 158.7, 165.4, 177.7

12b) 4-(2-(3-Fluoro-4-methoxyphenyl)-6,7-dihydro-5H-cyclopenta[d]pyrimidin-4-ylamino)benzoic acid ethyl ester Caesium carbonate (1.33 g, 4.09 mmol) and $PdCl_2(dppf)$ (1:1 complex with dichloromethane, 82 mg, 0.10 mmol) were added under an argon atmosphere to a solution of the chlorine compound 12a) (316 mg, 0.99 mmol) and 3-fluoro-4-methoxyphenyl boronic acid (156 mg, 0.99 mmol) in anhydrous 1,4-dioxane (4 ml) and the mixture was stirred first for 1.5 h at 90° C. and then for 16 h at room temperature. The reaction mixture was poured onto a silica gel column and the product was eluted with the following solvents [silica gel 60 (40 g); cyclohexane (200 ml), dichloromethane (500 ml), cyclohexane/ethyl acetate 1:1 (250 ml)]. White solid. Yield: 207 mg (51% of theoretical).

LC-MS (method 2): $R_f$=3.9 min, m/z: $[M+H]^+$=408.3
13C-NMR (101 MHz, DMSO-d6, δ ppm): 14.7, 21.7, 27.7, 34.4, 56.5, 60.7, 114.0, 114.9, 115.0, 117.0, 119.8, 123.3, 124.6, 124.6, 130.3, 131.6, 131.6, 145.1, 149.2, 149.3, 150.5, 152.9, 156.4, 160.8, 160.8, 165.9, 173.6

12c) 4-(2-(3-Fluoro-4-methoxyphenyl)-6,7-dihydro-5H-cyclopenta[d]pyrimidin-4-ylamino)benzoic acid 1N sodium hydroxide solution (1.57 ml, 1.57 mmol) was added to the ethyl ester 13b) (194 mg, 0.49 mmol) in methanol (5 ml) and 1,4-dioxane (3 ml) and the mixture was refluxed for 30 min while stirring, causing the initial suspension to change into a solution. After adding 1N hydrochloric acid (2.31 ml) a deposit was precipitated, which was filtered off, washed with water and diethyl ether and dried under vacuum. White solid. Yield: 166 mg (89% of theoretical). Melting point: >260° C.

LC-MS (method 2): $R_f$=3.5 min, m/z: $[M+H]^+$=380.2
13C-NMR (101 MHz, DMSO-d6, δ ppm): 21.2, 27.3, 33.9, 56.0, 113.5, 114.4, 116.4, 119.4, 123.8, 124.1, 130.0, 131.1, 131.2, 144.3, 148.7, 148.8, 150.1, 152.5, 156.0, 160.3, 160.3, 167.0, 173.1

EXAMPLE 13

4-(2-(3-Chloro-4-methoxyphenyl)-6,7-dihydro-5H-cyclopenta[d]pyrimidin-4-ylamino)benzoic acid (compound no. 14)

13a) 4-(2-(3-Chloro-4-methoxyphenyl)-6,7-dihydro-5H-cyclopenta[d]pyrimidin-4-ylamino)benzoic acid ethyl ester Produced in an analogous manner to procedure 12b) from the chlorine compound 12a) (318 mg, 1.00 mmol) and 3-chloro-4-methoxyphenyl boronic acid (186 mg, 1.00 mmol). White solid. Yield: 268 mg (63% of theoretical).
LC-MS (method 2): $R_t$=4.1 min, m/z: $[M+H]^+$=424.2
13C-NMR (101 MHz, DMSO-d6, δ ppm): 14.2, 21.1, 27.2, 33.9, 56.2, 60.2, 112.6, 116.5, 119.3, 121.0, 122.8, 127.6, 128.7, 129.8, 131.4, 144.6, 155.9, 160.1, 165.4, 173.1

13b) 4-(2-(3-Chloro-4-methoxyphenyl)-6,7-dihydro-5H-cyclopenta[d]pyrimidin-4-ylamino)benzoic acid The target compound was synthesised from the ethyl ester 13a) (229 mg, 0.54 mmol) in an analogous manner to procedure 12c). White solid. Yield: 194 mg (91% of theoretical). Melting point: >260° C.
LC-MS (method 2): $R_t$=3.7 min, m/z: $[M+H]^+$=396.2
13C-NMR (101 MHz, DMSO-d6, δ ppm): 21.2, 27.4, 33.2, 56.3, 112.7, 117.0, 120.1, 121.2, 124.6, 128.0, 129.0, 129.4, 130.0, 143.5, 156.3, 156.5, 158.8, 166.9, 170.3

EXAMPLE 14

4-(2-(3,4-Difluorophenyl)-6,7-dihydro-5H-cyclopenta[d]pyrimidin-4-ylamino)benzoic acid (compound no. 15)

14a) 4-(2-(3,4-Difluorophenyl)-6,7-dihydro-5H-cyclopenta[d]pyrimidin-4-ylamino)benzoic acid ethyl ester 4-(2-Chloro-6,7-dihydro-5H-cyclopenta[d]pyrimidin-4-ylamino)benzoic acid ethyl ester (318 mg, 1.00 mmol) and 3,4-difluorophenyl boronic acid (158 mg, 1.00 mmol) were reacted in an analogous manner to procedure 13b). White solid. Yield: 305 mg (77% of theoretical).
LC-MS (method 2): $R_t$=4.4 min, m/z: $[M+H]^+$=396.2
13C-NMR (101 MHz, DMSO-d6, δ ppm): 14.2, 21.1, 27.3, 33.8, 60.2, 115.9, 116.1, 117.2, 117.4, 117.6, 119.4, 122.9, 124.3, 124.4, 129.9, 135.7, 144.4, 148.1, 148.2, 149.4, 149.5, 150.5, 150.7, 151.9, 152.0, 156.0, 159.4, 165.4, 173.1

14b) 4-(2-(3,4-Difluorophenyl)-6,7-dihydro-5H-cyclopenta[d]pyrimidin-4-ylamino)benzoic acid Reaction of the ethyl ester 14a) (286 mg, 0.72 mmol) in an analogous manner to procedure 12c). White solid. Yield: 154 mg (58% of theoretical). Melting point: >260° C.
LC-MS (method 2): $R_t$=3.9 min, m/z: $[M+H]^+$=368.2
13C-NMR (101 MHz, DMSO-d6, δ ppm): 21.2, 27.3, 33.8, 115.9, 116.1, 117.1, 117.5, 117.6, 119.5, 124.0, 124.3, 124.4, 130.0, 135.6, 135.7, 135.7, 144.1, 148.1, 148.3, 149.4, 149.5, 150.6, 150.7, 151.9, 152.0, 156.1, 159.4, 167.0, 173.1

EXAMPLE 15

2-(4-(2-Phenyl-6,7-dihydro-5H-cyclopenta[d]pyrimidin-4-ylamino)phenyl)acetic acid (compound no. 16)

15a) 2-(4-(2-Chloro-6,7-dihydro-5H-cyclopenta[d]pyrimidin-4-ylamino)phenyl)acetic acid tert-butyl ester 2-(4-Aminophenyl)acetic acid tert-butyl ester (2.00 g, 9.66 mmol) and 2,4-dichloro-6,7-dihydro-5H-cyclopenta[d]pyrimidine (1.74 g, 9.20 mmol) in NMP (46 ml) were stirred overnight at 80° C. After cooling to room temperature, ethyl acetate (200 ml) was added, the mixture was washed with water and dried with magnesium sulfate. The solvent was distilled off and the residue stirred with methanol and hexane. The solid was filtered and dried under vacuum. Brown solid. Yield: 1.3 g (39% of theoretical).

15b) 2-(4-(2-Phenyl-6,7-dihydro-5H-cyclopenta[d]pyrimidin-4-ylamino)phenyl)acetic acid The pyrimidine from 16a) (36 mg, 0.100 mmol), phenyl boronic acid (15 mg, 0.120 mmol), caesium carbonate (49 mg, 0.150 mmol) and tetrakis(triphenylphosphine)palladium(0) (5.8 mg, 0.005 mmol) were heated in an acetonitrile/water mixture (1.3 ml, 3:1) to 125° C. for 30 min in a microwave reactor. After cooling to room temperature the mixture was diluted with water and extracted with dichloromethane. The combined organic phases were concentrated to small volume and the residue (51 mg) was mixed with trifluoroacetic acid/water (1.0 ml, 9:1) and stirred at room temperature for 1 h. Then the trifluoroacetic acid was removed under vacuum and the crude product was purified by column chromatography. White solid.
LC-MS (method 1): $R_t$=1.34 min, m/z: $[M+H]^+$=346, $[M+H]^-$=344

EXAMPLE 16

2-(4-(2-(3-Fluorophenyl)-6,7-dihydro-5H-cyclopenta[d]pyrimidin-4-ylamino)phenyl)acetic acid (compound no. 17)

16a) 2-(4-(2-(3-Fluorophenyl)-6,7-dihydro-5H-cyclopenta[d]pyrimidin-4-ylamino)phenyl)acetic acid tert-butyl ester Produced from 2-(4-(2-chloro-6,7-dihydro-5H-cyclopenta[d]pyrimidin-4-ylamino)phenyl)acetic acid tert-butyl ester (108 mg, 0.30 mmol) and 3-fluorophenyl boronic acid (50 mg, 0.36 mmol) in an analogous manner to procedure 15b). White solid.
LC-MS (method 1): $R_t$=1.6 min, m/z: $[M+H]^+$=364 ($ES^+$)

EXAMPLE 17

2-(4-(2-(4-Bromophenyl)-6,7-dihydro-5H-cyclopenta[d]pyrimidin-4-ylamino)phenyl)acetic acid (compound no. 1)

17a) 2-(4-Bromophenyl)-6,7-dihydro-5H-cyclopenta[d]pyrimidin-4-ol

Methyl-2-oxocyclopentane carboxylate (3.12 ml, 25.1 mmol) was added dropwise at room temperature to a solution of 4-bromobenzimidamide (5.00 g, 25.1 mmol) in dioxane (170 ml). Then the reaction mixture was stirred overnight at 90° C. After cooling, the precipitated solid was separated off, washed with diethyl ether and dried. Beige solid. Yield: 2.20 g (30% of theoretical).

LC-MS (method 3): $R_t$=0.60 min, m/z: $[M+H]^+$=291.0/293.0

17b) 2-(4-Bromophenyl)-4-chloro-6,7-dihydro-5H-cyclopenta[d]pyrimidine 2-(4-Bromophenyl)-6,7-dihydro-5H-cyclopenta[d]pyrimidin-4-ol (3.00 g, 11.9 mmol) and phosphorus oxychloride (44 ml) were stirred under a protective gas atmosphere at 90° C. for 3 h. After cooling, the mixture was slowly introduced into iced water while stirring. It was neutralised with Na$_2$CO$_3$ and NaHCO$_3$ and then extracted with dichloromethane. The combined organic phases were dried with magnesium sulfate and concentrated to small volume. The residue was suspended with 20 ml diethyl ether, filtered, washed with 10 ml diethyl ether and then purified by chromatography [silica gel, hexane/ethyl acetate=9:1]. Light-grey solid. Yield: 2.20 g (60% of theoretical).

LC-MS (method 3): $R_t$=1.00 min, m/z: $[M+H]^+$=309.0/311.0

17c) 2-(4-(2-(4-Bromophenyl)-6,7-dihydro-5H-cyclopenta[d]pyrimidin-4-ylamino)phenyl)acetic acid methyl ester 2-(4-Bromophenyl)-4-chloro-6,7-dihydro-5H-cyclopenta[d]pyrimidine (1.00 g, 3.23 mmol) and methyl (4-aminophenyl)acetate (0.64 g, 3.88 mmol), caesium carbonate (2.63 g, 8.08 mmol), BINAP (300 mg, 0.49 mmol) and palladium (II) acetate (70 mg, 0.32 mmol) were stirred in anhydrous 1,4-dioxane (35 ml) under a protective gas atmosphere at 90° C. for 24 h. Then ethyl acetate was added to the reaction mixture, it was washed with water and dried with magnesium sulfate. After concentration to small volume the residue was purified by column chromatography [silica gel, dichloromethane/diethyl ether=50:1]. Light-brown solid. Yield: 250 mg (18% of theoretical)

LC-MS (method 3): $R_t$=0.78 min, m/z: $[M+H]^+$=438.1/440.1

17d) 2-(4-(2-(4-Bromophenyl)-6,7-dihydro-5H-cyclopenta[d]pyrimidin-4-ylamino)phenyl)acetic acid The product from procedure 17c) (240 mg, 0.548 mmol) and lithium hydroxide (26 mg, 1.096 mmol) were stirred in a THF/water mixture (2:1, 1.8 ml) at room temperature for 24 h. Then the mixture was diluted with 5 ml water, adjusted to pH 1-2 with 1M hydrochloric acid and extracted with dichloromethane/THF (4:1). The combined organic phases were washed with saturated sodium chloride solution, dried with magnesium sulfate, filtered and concentrated to small volume. The beige solid thus obtained was freed from solvent residues under vacuum. Yield: 220 mg (95% of theoretical).

LC-MS (method 3): $R_t$=0.64 min, m/z: $[M+H]^+$=424.1/426.1

EXAMPLE 18

2-(4-(2-(3-Bromophenyl)-6,7-dihydro-5H-cyclopenta[d]pyrimidin-4-ylamino)phenyl)acetic acid (compound no. 18)

Produced in an analogous manner to Example 17. Solid product.

LC-MS (method 3): $R_t$=0.66 min, m/z: $[M+H]^+$=424.1/426.1

EXAMPLE 19

2-(4-(2-(Benzofuran-5-yl)-6,7-dihydro-5H-cyclopenta[d]pyrimidin-4-ylamino)phenyl)acetic acid (compound no. 2-1)

19a) 2-(4-(2-(Benzofuran-5-yl)-6,7-dihydro-5H-cyclopenta[d]pyrimidin-4-ylamino)phenyl)acetic acid tert-butylester Produced in an analogous manner to Example 1c) from 2-(4-(2-chloro-6,7-dihydro-5H-cyclopenta[d]pyrimidin-4-ylamino)phenyl)acetic acid tert-butylester (250 mg, 0,695 mmol) and benzofuran-5-ylboronic acid (168 mg, 1,043 mmol). Yield: 200 mg (65% of theoretical).

LC-MS (method 3): $R_t$=0.79 min, m/z: $[M+H]^+$=442.2

19b) 2-(4-(2-(Benzofuran-5-yl)-6,7-dihydro-5H-cyclopenta[d]pyrimidin-4-ylamino)phenyl) acetic acid The product obtained by procedure 19a) (200 mg, 0,453 mmol) was treated with formic acid (1.4 ml; 98-100% ig) and stirred 3 days at room temperature. The formic acid was removed under vacuum. Methanol (3 ml) and diethylether (3 ml) were added to the remnant whereas a precipitation occurred. The precipitate was separated, washed with diethylether and dried under ultra-high vacuum conditions. White solid. Yield: 93 mg (53% of theoretical).

LC-MS (method 3): $R_t$=0.52 min, m/z: $[M+H]^+$=386.2

EXAMPLE 20

4-(2-(3-Chlorophenyl)-5,6,7,8-tetrahydroquinazoline-4-ylamino)benzoic acid (compound no. 19)

20a) 4-(2-(3-Chlorophenyl)-5,6,7,8-tetrahydrochinazolin-4-ylamino)benzoic acid methylester Produced in an analogous manner to Example 10a) from 4-chloro-2-(3-chlorophenyl)-5,6,7,8-tetrahydroquinazoline (81 mg, 0.29 mmol) and 4-aminobenzoic acidmethylester (46 mg, 0.30 mmol). Colorless solid. Yield: 65 mg (62% of theoretical).

LC-MS (method 1): $R_t$=2.62 min, m/z: $[M+H]^+$=394.2/396.2, $[M-H]^-$=392.1/394.1

20b) 4-(2-(3-Chlorophenyl)-5,6,7,8-tetrahydroquinazoline-4-ylamino)benzoic acid The product obtained by procedure 20a) was reacted in analogous manner to Example 10b). Deviating from this procedure, the target compound was purified by precipitation as hydrochloride salt. Yield: 58 mg (82% of theoretical; hydrochloride).

LC-MS (method 1): $R_t$=2.04 min, m/z: $[M+H]^+$=380.2/382.2, $[M-H]^-$=378.1/380.2

TABLE 4

Physico chemical data:

| Compound No. | Physico-chemical data |
|---|---|
| 20 | LC-MS (method 1): $R_t$ = 1.40 min, m/z: $[M+H]^+$ = 376 |
| 21 | LC-MS (method 1): $R_t$ = 1.88 min, m/z: $[M+H]^+$ = 414 |
| 22 | LC-MS (method 1): $R_t$ = 1.73 min, m/z: $[M+H]^+$ = 371 |
| 23 | LC-MS (method 1): $R_t$ = 1.50 min, m/z: $[M+H]^+$ = 360 |
| 2-2 | LC-MS (method 3): $R_t$ = 0.57 min, m/z: $[M+H]^+$ = 390.2 |
| 2-3 | LC-MS (method 3): $R_t$ = 0.48 min, m/z: $[M+H]^+$ = 397.2 |
| 2-4 | LC-MS (method 3): $R_t$ = 0.45 min, m/z: $[M+H]^+$ = 347.2 |
| 2-5 | LC-MS (method 3): $R_t$ = 0.49 min, m/z: $[M+H]^+$ = 388.2 |
| 2-6 | LC-MS (method 1): $R_t$ = 2.27 min, m/z: $[M+H]^+$ = 394 |
| 3-1 | LC-MS (method 1): $R_t$ = 1.59 min, m/z: $[M+H]^+$ = 366 |
| 3-2 | LC-MS (method 1): $R_t$ = 1.78 min, m/z: $[M+H]^+$ = 394.2/396.2.2, $[M-H]^-$ = 392.1/394.0 |
| 3-3 | LC-MS (method 1): $R_t$ = 1.82 min, m/z: $[M+H]^+$ = 380.2/382.1, $[M-H]^-$ = 378.0/380.1 |
| 3-4 | LC-MS (method 1): $R_t$ = 2.10 min, m/z: $[M+H]^+$ = 408.2/410.2, $[M-H]^-$ = 406.1/408.1 |

BIOLOGICAL ACTIVITIES

A. Biological Activity of the Compounds According to the Invention

1. Determination of the PDE4B IC50 Values with a cAMP HRTF® Assay to Determine the Activity of hPDE4B1

The inhibiting effect of the compounds on the enzyme activity of human PDE4B1 is measured by the quantification of 5'-AMP, which is formed from 3',5'-adenosine monophosphate (cAMP). Human recombinant enzyme, expressed in Sf9 cells, and the HTRF (homogeneous time-resolved fluorescence) detection method are used in the assay.

The test compound or water (control) is mixed with the human recombinant PDE4B1 enzyme (4.8 U) in a buffer consisting of 44.4 mM tris-HCl, 5.28 mM MgCl2, 2.64 mM DTT and 0.044% Tween 20 (pH 7.8). After adding the cAMP enzyme substrate (final concentration 40 nM) the mixture is incubated for 30 minutes at room temperature. Then a fluorescence acceptor (Dye2 marked with cAMP), a fluorescence donor (anti-cAMP antibody marked with a europium cryptate) and the non-specific phosphodiesterase inhibitor IBMX (3-isobutyl-1-methylxanthine; final concentration 1 mM) are added. After 60 minutes the fluorescence transfer, which correlates with the amount of remaining cAMP, is measured with a microplate reader (Rubystar, BMG) at λex=337 nm, λem=620 nm and λem=665 nm. The enzyme activity is calculated from the quotient formed from the measured signal at 665 nm and that at 620 nm. The result is expressed as the percentage inhibition of enzyme activity of the control (without PDE4 inhibitor) (literature: N. Saldou et al., Comparison of recombinant human PDE4 isoforms: interaction with substrate and inhibitors, Cell. Signal. Vol. 10, No. 6, 427-440, 1998). The enzyme is omitted for measurement of the basal control. The averaged results are set out in Table 5.

2. Determination of the PDE4D-IC50 Values with a cAMP HRTF® Assay to Determine the Activity of hPDE4D2

The test compound or water are mixed with the human recombinant PDE4D2 enzyme (0.75 U) in HBSS buffer (Invitrogen), to which 1.5 mM $MgCl_2$ and 1% BSA (bovine serum albumin) have additionally been added. The further procedure and evaluation are performed in exactly the same way as in the above description of the cAMP HTRF® assay for PDE4B.

TABLE 5

| Compound no. | PDE4B IC50 [μM] |
|---|---|
| 1 | 0.66 |
| 2 | 0.19 |
| 3 | 0.12 |
| 4 | 0.07 |
| 5 | 0.49 |
| 6 | 3.10 |
| 7 | 0.60 |
| 8 | 0.38 |
| 9 | 0.88 |
| 10 | 0.30 |
| 11 | 0.64 |
| 12 | 0.55 |
| 13 | 0.21 |
| 14 | 0.14 |
| 15 | 0.39 |
| 16 | 0.69 |
| 17 | 0.21 |
| 18 | 0.22 |
| 2-1 | 0.74 |
| 19 | 2.14 |

2. Determination of the Selectivity from the Quotient of the 1050 Valus for PDE4D and PDE4B $$\frac{IC_{50} PDE4D}{IC_{50} PDE4B} = \text{Measure of } PDE4B \text{ selectivity}$$

The 1050 value for PDE4D was determined as described above.

The 1050 PDE4B values listed in Table 5 and the PDE4D IC050 values determined by the aforementioned method were used to calculate the quotient.

A quotient of over 10 was calculated for the following compounds: 2, 5, 7, 8, 10, 14 and 17.

A quotient of over 50 was calculated for the following compounds: 3 and 4.

B. Comparative Experiments

Compound no. 28 (referred to hereafter as compound no. S1) and compound no. 1 (referred to hereafter as compound no. S2) from Kenji et al. (2009) (in Bioorganic & Medicinal Chemistry Letters 19 (2009) p. 3174-3176) were re-synthesised and tested in the cAMP HTRF® assays.

Compound no. S1

(= no. 28 in Kenji et al. (2009))

Compound no. S2

(= no. 1 in Kenji et al. (2009))

The following results were obtained:

TABLE 6

| Compound no. | PDE4B IC50 [µM] | PDE4D IC50 [µM] | Quotient of IC50 4D/4B |
|---|---|---|---|
| S1 | 3.6 | >10 | >2.8 |
| S2 | 1.1 | 1.3 | 1.2 |

The invention claimed is:

1. Pyrimidine compounds of general formula (I)

$$\text{(I)}$$

in which

G denotes a phenyl optionally substituted with at least one substituent Z or a 6-membered heteroaromatic optionally substituted with at least one substituent Z; or denotes a phenyl optionally substituted with at least one substituent Z or a 6-membered heteroaromatic optionally substituted with at least one substituent Z, being part of a 8- to 10-membered heterocyclic condensed ring containing at least one heteroatom selected from N, O, and S;

Z independently of one another denotes $(C_1\text{-}C_6)$ alkyl, $(C_1\text{-}C_6)$ hydroxyalkyl, $(C_1\text{-}C_6)$ alkoxy, $(C_1\text{-}C_6)$ haloalkyl, $(C_1\text{-}C_6)$ haloalkoxy, —S$(C_1\text{-}C_6)$ alkyl, halogen, hydroxyl or cyano, wherein aforementioned alkyls are branched or straight-chain and can be substituted;

Q denotes a phenyl, pyrimidyl, or pyrazinyl substituted with a substituent $X^1$ and optionally substituted with at least one substituent X;

X independently of one another denotes $(C_1\text{-}C_6)$ alkyl, $(C_3\text{-}C_6)$ cycloalkyl, $(C_1\text{-}C_6)$ alkoxy, $(C_3\text{-}C_6)$ cycloalkoxy, $(C_1\text{-}C_6)$ haloalkyl, $(C_1\text{-}C_6)$ haloalkoxy, halogen, hydroxyl, cyano, carboxyl, —NH$_2$, —NH$(C_1\text{-}C_6)$ alkyl, —N$((C_1\text{-}C_6)$ alkyl$)_2$, N-pyrrolidinyl, N-piperidinyl, N-morpholinyl, —NH—C(O)—$(C_1\text{-}C_6)$ alkyl, —C(O)—NH$_2$, —C(O)—NH$(C_1\text{-}C_6)$ alkyl, —C(O)—N$((C_1\text{-}C_6)$ alkyl$)_2$, —S(O)$_2$—NH$_2$, —S$(C_1\text{-}C_6)$ alkyl, —S(O)—$(C_1\text{-}C_6)$ alkyl, or —S(O)$_2$—$(C_1\text{-}C_6)$ alkyl, wherein the aforementioned alkyl chains are branched or straight-chain and can be substituted;

$X^1$ denotes an L-CO$_2$R$^2$ group;

L denotes a bond, $(C_1\text{-}C_6)$ alkylene, $(C_2\text{-}C_6)$ alkenylene, —O—$(C_1\text{-}C_4)$alkylene, —NH—$(C_1\text{-}C_4)$ alkylene, or —NR$^3$—$(C_1\text{-}C_4)$ alkylene, wherein aforementioned alkylenes or alkenylenes can each be substituted with one or more halogen atoms or wherein aforementioned alkylenes or alkenylenes can be substituted with one or more $(C_1\text{-}C_6)$ alkyl groups, or wherein in aforementioned alkylenes or alkenylenes a CH$_2$ unit can be replaced by an oxygen atom;

R$^1$ denotes hydrogen or a branched or straight-chain $(C_1\text{-}C_6)$ alkyl;

R$^2$ and R$^3$, independently of each other denotes hydrogen or a branched or straight-chain $(C_1\text{-}C_6)$ alkyl;

n denotes 1 or 2;

K denotes $(C_1\text{-}C_6)$ alkyl, $(C_1\text{-}C_6)$ alkoxy, $(C_1\text{-}C_6)$ haloalkyl, halogen, hydroxyl or cyano; and m denotes 0, 1, 2, 3 or 4, as well as pharmacologically tolerable salts, diastereomers, enantiomers, racemates, hydrates or solvates thereof.

2. The pyrimidine compounds according to claim 1, wherein

Z independently of one another denotes CH3, OCH3, CF3, CHF2, CH2F, OCF3, OCHF2, OCH2F, SCH3, Cl, F, OH or CN;

X1 denotes an L-CO2R2 group;

L denotes a bond or methylene, wherein the methylene can be substituted with one or two halogen atoms; and R1 denotes hydrogen or a branched or straight-chain (C1-C4) alkyl;

R2 denotes hydrogen or a branched or straight-chain (C1-C4) alkyl;

K denotes (C1-C4) alkyl, (C1-C4) alkoxy, (C1-C4) haloalkyl, fluorine, chlorine, bromine, hydroxyl or cyano.

3. The pyrimidine compounds according to claim 1, wherein

G denotes a phenyl optionally substituted with at least one substituent Z or a 6-membered heteroaromatic optionally substituted with at least one substituent Z, selected from the following groups G1 to G9;

G1

G2

-continued
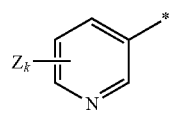 G3
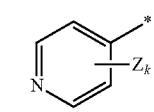 G4
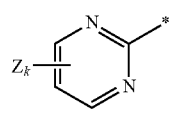 G5
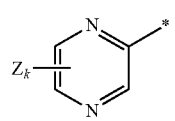 G6
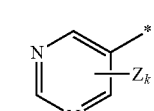 G7
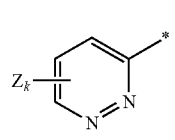 G8
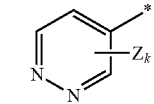 G9
in which the site marked with an asterisk (*) indicates the binding site at position 2 of the pyrimidine ring;
k denotes 0, 1 or 2; and
Q is selected from the following groups Q1 to Q13,
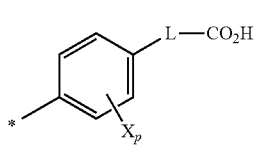 Q1
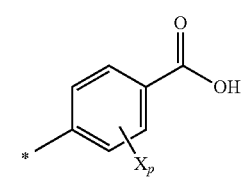 Q2
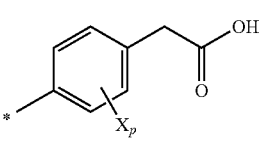 Q3
-continued
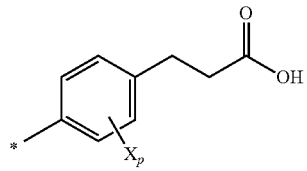 Q4
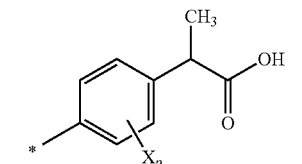 Q5
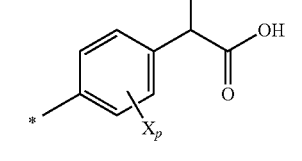 Q6
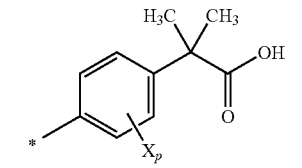 Q7
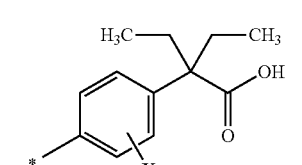 Q8
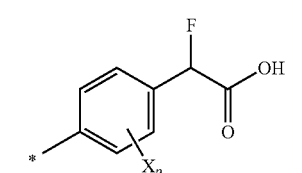 Q9
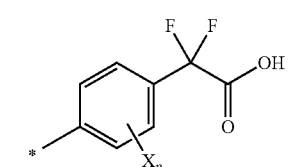 Q10
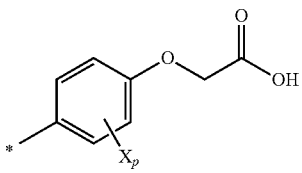 Q11
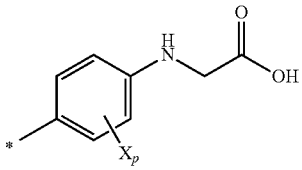 Q12

-continued

Q13

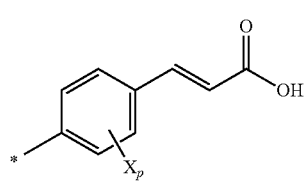

in which the site marked with an asterisk (*) indicates the binding site at the nitrogen and
p denotes 0, 1, 2, 3 or 4;
X independently of one another denotes (C1-C6) alkyl, (C3-C6) cycloalkyl, (C1-C6) alkoxy, (C3-C6) cycloalkoxy, (C1-C6) haloalkyl, (C1-C6) haloalkoxy, halogen, hydroxyl, cyano, carboxyl, —NH2, —NH(C1-C6) alkyl, —N((C1-C6) alkyl)2, N-pyrrolidinyl, N-piperidinyl, N-morpholinyl, —NH—C(O)—(C1-C6) alkyl, —C(O)—NH2, —C(O)—NH(C1-C6) alkyl, —C(O)—N((C1-C6) alkyl)2, —S(O)2-NH2, —S(C1-C6) alkyl, —S(O)—(C1-C6) alkyl, or —S(O)2-(C1-C6) alkyl, wherein the aforementioned alkyl chains are branched or straight-chain and can be substituted;
L denotes a bond or methylene, wherein the methylene can be substituted with one or two halogen atoms.

4. The pyrimidine compounds according to claim 1, wherein n denotes 1.

5. The pyrimidine compounds according to claim 1, wherein n denotes 2.

6. The pyrimidine compounds according to claim 1, wherein m denotes 0.

7. The pyrimidine compounds according to claim 1, wherein p denotes 0 or 1.

8. The pyrimidine compounds according to claim 3, wherein
G denotes a phenyl optionally substituted with at least one substituent Z or a 6-membered heteroaromatic optionally substituted with at least one substituent Z, selected from G1, G2, G3 or G4; and
Q denotes a chemical grouping Q2, Q3, Q8 or Q9.

9. The pyrimidine compounds according to claim 3, wherein
G denotes a phenyl G1 optionally substituted with at least one substituent Z; and
Q denotes a chemical grouping Q1, Q2 or Q3.

10. The pyrimidine compounds according to claim 3, wherein
G denotes a phenyl G1 optionally substituted with at least one substituent Z; and
Q denotes a chemical grouping Q2.

11. The pyrimidine compounds according to claim 3, wherein
G denotes a phenyl G1 optionally substituted with at least one substituent Z; and
Q denotes a chemical grouping Q3.

12. A pharmaceutical composition comprising at least one compound as defined in claim 1.

13. A method of treating conditions or diseases responsive to the inhibition of PDE4-enzyme, said method comprising administering to a patient in need thereof an effective amount of one or more compounds as defined in claim 1, or a physiologically tolerable salt thereof, or a pure stereoisomer thereof, wherein said conditions or diseases are selected from the following group:
inflammatory diseases of the joints selected from rheumatoid arthritis, psoriatic arthritis, ankylosing spondylitis (Bechterew's disease), gout and osteoarthritis;
inflammatory diseases of the skin selected from psoriasis, atopic dermatitis and lichen planus;
inflammatory diseases of the eyes selected from uveitis;
gastrointestinal diseases and complaints selected from inflammatory diseases of the digestive organs, Crohn's disease, ulcerative colitis, and acute and chronic inflammations of the gall bladder, bile ducts, pseudopolyps and juvenile polyps;
inflammatory diseases of the internal organs selected from SLE (systemic lupus erythematosus), lupus nephritis, chronic prostatitis and interstitial cystitis;
hyperplastic diseases selected from benign prostatic hyperplasia;
respiratory or lung diseases associated with elevated mucus production, inflammation and/or obstruction of the respiratory tract selected from: COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis and pneumonia;
diseases of the fibrotic spectrum selected from hepatic fibrosis, systemic sclerosis and scleroderma;
cancers selected from haematopoietic cancers, B-cell lymphomas, T-cell lymphomas, chronic lymphatic and chronic myeloid leukaemia, acute lymphatic and acute myeloid leukaemia, and gliomas;
metabolic diseases selected from type 2 diabetes, metabolic syndrome, obesity/adiposity and fatty liver disease (not alcohol-induced);
cardiovascular diseases selected from: arteriosclerosis and pulmonary arterial hypertension;
psychological disorders selected from: schizophrenia, depression, bipolar or manic depression, dementia, memory loss and generalized anxiety disorder (GAD); and
diseases of the peripheral or central nervous system selected from Parkinson's disease, multiple sclerosis, Alzheimer's disease, stroke and amyotrophic lateral sclerosis.

* * * * *

UNITED STATES PATENT AND TRADEMARK OFFICE
CERTIFICATE OF CORRECTION

PATENT NO. : 9,505,724 B2
APPLICATION NO. : 14/817683
DATED : November 29, 2016
INVENTOR(S) : Konetzki et al.

It is certified that error appears in the above-identified patent and that said Letters Patent is hereby corrected as shown below:

In the Specification

Column 4, Group G1, "$//_4^4$" -- should read -- $//_4^5$ --.

Column 9, Line 44, "on" -- should read -- one --.

Column 29, Line 44, "-4-ylamino)" -- should read -- -4-yl)amino) --.

Column 30, Line 34, "cyclopenta[a]pyrimidin" -- should read -- cyclopenta[d]pyrimidin --.

Column 40, Line 43, "1050" -- should read -- IC50 --.

Column 40, Line 50, "1050" -- should read -- IC50 --.

Column 40, Line 52, "1050" -- should read -- IC50 --.

Column 40, Line 53, "1050" -- should read -- IC50 --.

In the Claims

Column 42, Group G1, "$_4//^4$" -- should read -- $//_4^5$ --.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*